United States Patent
Friedman et al.

(10) Patent No.: US 9,668,671 B2
(45) Date of Patent: *Jun. 6, 2017

(54) ENHANCED SIGNAL NAVIGATION AND CAPTURE SYSTEMS AND METHODS

(71) Applicants: MAYO FOUNDATION FOR MEDICAL EDUCATION AND RESEARCH, Rochester, MN (US); AEGIS MEDICAL INNOVATIONS INC., Vancouver (CA)

(72) Inventors: Paul A. Friedman, Rochester, MN (US); Charles J. Bruce, Rochester, MN (US); Samuel J. Asirvatham, Rochester, MN (US); Trevor A. McCaw, Vancouver (CA); Elliot Y. K. Hong, Vancouver (CA)

(73) Assignees: MAYO FOUNDATION FOR MEDICAL EDUCATION AND RESEARCH, Rochester, MN (US); AEGIS MEDICAL INNOVATIONS INC., Vancouver, B.C. (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/867,509

(22) Filed: Sep. 28, 2015

(65) Prior Publication Data

US 2016/0015294 A1 Jan. 21, 2016

Related U.S. Application Data

(63) Continuation of application No. 13/499,431, filed as application No. PCT/US2010/050835 on Sep. 30, 2010, now Pat. No. 9,144,431.

(Continued)

(51) Int. Cl.
*H04N 7/18* (2006.01)
*A61B 5/06* (2006.01)
(Continued)

(52) U.S. Cl.
CPC ............ *A61B 5/068* (2013.01); *A61B 5/0422* (2013.01); *A61B 5/6859* (2013.01);
(Continued)

(58) Field of Classification Search
CPC . A61B 17/12013; A61B 17/29; A61B 5/0402; A61B 2017/00243
(Continued)

(56) References Cited

U.S. PATENT DOCUMENTS

| 4,041,952 A | 8/1977 | Morrison, Jr. et al. |
| 5,026,370 A | 6/1991 | Lottick |

(Continued)

FOREIGN PATENT DOCUMENTS

| EP | 0 775 466 A2 | 5/1997 |
| WO | WO 2008/036408 A3 | 9/2008 |

(Continued)

OTHER PUBLICATIONS

International Search Report mailed Jun. 15, 2011, in Korea, Patent Application No. PCT/US2010/050835, filed Sep. 30, 2010.
(Continued)

*Primary Examiner* — Brian Yenke
*Assistant Examiner* — Jean W Desir
(74) *Attorney, Agent, or Firm* — Mueting, Raasch & Gebhardt, P.A.

(57) ABSTRACT

Navigation and tissue capture systems and methods for navigation to and/or capture of selected tissue using the innate electrical activity of the selected tissue and/or other tissue are described. In the context of left atrial appendage closure, the systems and methods can be used to navigate to the left atrial appendage and capture/control the appendage while a closure instrument (suture, clip, ring) is placed over the appendage and tightened down or a closure method (ablation, cryogenic procedures, stapling, etc.) is performed
(Continued)

to close the left atrial appendage. The use of innate electrical activity for navigating devices may be used in connection with other tissues and/or areas of the body.

13 Claims, 16 Drawing Sheets

Related U.S. Application Data

(60) Provisional application No. 61/247,276, filed on Sep. 30, 2009.

(51) Int. Cl.
  *A61B 17/12* (2006.01)
  *A61B 17/29* (2006.01)
  *A61B 5/042* (2006.01)
  *A61B 5/00* (2006.01)
  *A61B 5/0402* (2006.01)
  *A61B 17/00* (2006.01)
  *A61B 17/30* (2006.01)
  *A61B 90/00* (2016.01)

(52) U.S. Cl.
  CPC ........ *A61B 17/12013* (2013.01); *A61B 17/29* (2013.01); *A61B 5/0402* (2013.01); *A61B 2017/00026* (2013.01); *A61B 2017/00243* (2013.01); *A61B 2017/2926* (2013.01); *A61B 2017/2947* (2013.01); *A61B 2017/308* (2013.01); *A61B 2090/065* (2016.02)

(58) Field of Classification Search
  USPC ........ 348/65, 45, 61, 77; 606/206, 207, 205, 606/21, 46; 600/509, 372
  See application file for complete search history.

(56) References Cited

U.S. PATENT DOCUMENTS

| | | | |
|---|---|---|---|
| 5,306,234 A | 4/1994 | Johnson | |
| 5,318,589 A | 6/1994 | Lichtman | |
| 5,403,331 A | 4/1995 | Chesterfield et al. | |
| 5,713,896 A | 2/1998 | Nardella | |
| 5,755,717 A | 5/1998 | Yates et al. | |
| 5,865,791 A | 2/1999 | Whayne et al. | |
| 5,957,863 A | 9/1999 | Koblish et al. | |
| 6,068,629 A | 5/2000 | Haissaguerre et al. | |
| 6,120,496 A | 9/2000 | Whayne et al. | |
| 6,206,827 B1 | 3/2001 | Chin et al. | |
| 6,261,242 B1 | 7/2001 | Roberts et al. | |
| 6,488,689 B1 | 12/2002 | Kaplan et al. | |
| 6,666,861 B1 | 12/2003 | Grabeck | |
| 6,669,687 B1 | 12/2003 | Saadat | |
| 6,743,225 B2 | 6/2004 | Sanchez et al. | |
| 6,771,996 B2 | 8/2004 | Bowe et al. | |
| 6,786,905 B2 | 9/2004 | Swanson et al. | |
| 6,887,240 B1 | 5/2005 | Lands et al. | |
| 6,899,710 B2 | 5/2005 | Hooven | |
| 6,932,811 B2 | 8/2005 | Hooven et al. | |
| 7,141,057 B2 | 11/2006 | Burbank et al. | |
| 7,214,180 B2 | 5/2007 | Chin | |
| 7,226,458 B2 | 6/2007 | Kaplan et al. | |
| 7,276,235 B2 | 10/2007 | Metzner et al. | |
| 7,338,434 B1 | 3/2008 | Haarstad et al. | |
| 7,347,856 B2 * | 3/2008 | Wittenberger | A61B 17/2812 606/20 |
| 7,398,781 B1 | 7/2008 | Chin | |
| 7,468,061 B2 | 12/2008 | Hooven et al. | |
| 7,527,634 B2 | 5/2009 | Zenati et al. | |
| 7,697,972 B2 | 4/2010 | Verard et al. | |
| 7,828,810 B2 | 11/2010 | Liddicoat et al. | |
| 7,846,168 B2 | 12/2010 | Liddicoat et al. | |
| 7,918,865 B2 | 4/2011 | Liddicoat et al. | |
| 7,938,823 B2 | 5/2011 | Wittenberger et al. | |
| 7,957,820 B2 * | 6/2011 | Bertolero | A61B 1/12 607/129 |
| 8,628,522 B2 * | 1/2014 | Ibrahim | 606/32 |
| 9,144,431 B2 * | 9/2015 | Friedman | A61B 17/12013 |
| 9,198,683 B2 * | 12/2015 | Friedman | A61B 17/12013 |
| 2002/0151889 A1 | 10/2002 | Swanson et al. | |
| 2002/0177765 A1 | 11/2002 | Bowe et al. | |
| 2003/0163128 A1 | 8/2003 | Patil et al. | |
| 2004/0015163 A1 | 1/2004 | Buysse et al. | |
| 2004/0030335 A1 | 2/2004 | Zenati et al. | |
| 2004/0044340 A1 | 3/2004 | Francischelli et al. | |
| 2004/0064138 A1 | 4/2004 | Grabek | |
| 2004/0097805 A1 | 5/2004 | Verard et al. | |
| 2004/0102804 A1 | 5/2004 | Chin | |
| 2005/0090728 A1 | 4/2005 | Mest | |
| 2005/0154404 A1 | 7/2005 | Liddicoat et al. | |
| 2006/0229594 A1 | 10/2006 | Francischelli et al. | |
| 2006/0253129 A1 | 11/2006 | Liddicoat et al. | |
| 2006/0271038 A1 | 11/2006 | Johnson et al. | |
| 2007/0073313 A1 | 3/2007 | Liddicoat et al. | |
| 2007/0164900 A1 | 7/2007 | Schneider et al. | |
| 2008/0033456 A1 | 2/2008 | Cantanese et al. | |
| 2008/0058657 A1 | 3/2008 | Schwartz et al. | |
| 2008/0058845 A1 | 3/2008 | Shimizu et al. | |
| 2008/0097139 A1 | 4/2008 | Clerc et al. | |
| 2008/0125795 A1 | 5/2008 | Kaplan et al. | |
| 2008/0147097 A1 | 6/2008 | Liddicoat et al. | |
| 2008/0172052 A1 | 7/2008 | Eder et al. | |
| 2008/0221593 A1 | 9/2008 | Liddicoat et al. | |
| 2008/0243183 A1 | 10/2008 | Miller et al. | |
| 2008/0255470 A1 | 10/2008 | Hauck et al. | |
| 2008/0294175 A1 | 11/2008 | Bardsley et al. | |
| 2009/0036881 A1 | 2/2009 | Artale et al. | |
| 2009/0143791 A1 | 6/2009 | Miller et al. | |
| 2009/0157118 A1 | 6/2009 | Miller et al. | |
| 2009/0171304 A1 | 7/2009 | Cao et al. | |
| 2010/0069925 A1 | 3/2010 | Friedman et al. | |
| 2011/0112569 A1 | 5/2011 | Friedman et al. | |
| 2012/0330351 A1 | 12/2012 | Friedman et al. | |
| 2015/0088019 A1 * | 3/2015 | MacAdam | A61B 5/046 600/518 |

FOREIGN PATENT DOCUMENTS

| | | | |
|---|---|---|---|
| WO | WO 2008/036408 A2 | 3/2009 | |
| WO | WO 2009/120953 A2 | 10/2009 | |

OTHER PUBLICATIONS

Written Opinion mailed Jun. 15, 2011, in Korea, Patent Application No. PCT/US2010/050835, filed Sep. 30, 2010.
International Preliminary Report on Patentability issued Apr. 3, 2012, in Switzerland, Patent Application No. PCT/US2010/050835, filed Sep. 30, 2010.
[Europe] Patent Application No. 10 82 1218.4, filed Sep. 30, 2010; [Extended Search Report] issued Feb. 23, 2017; 6 pages.

* cited by examiner

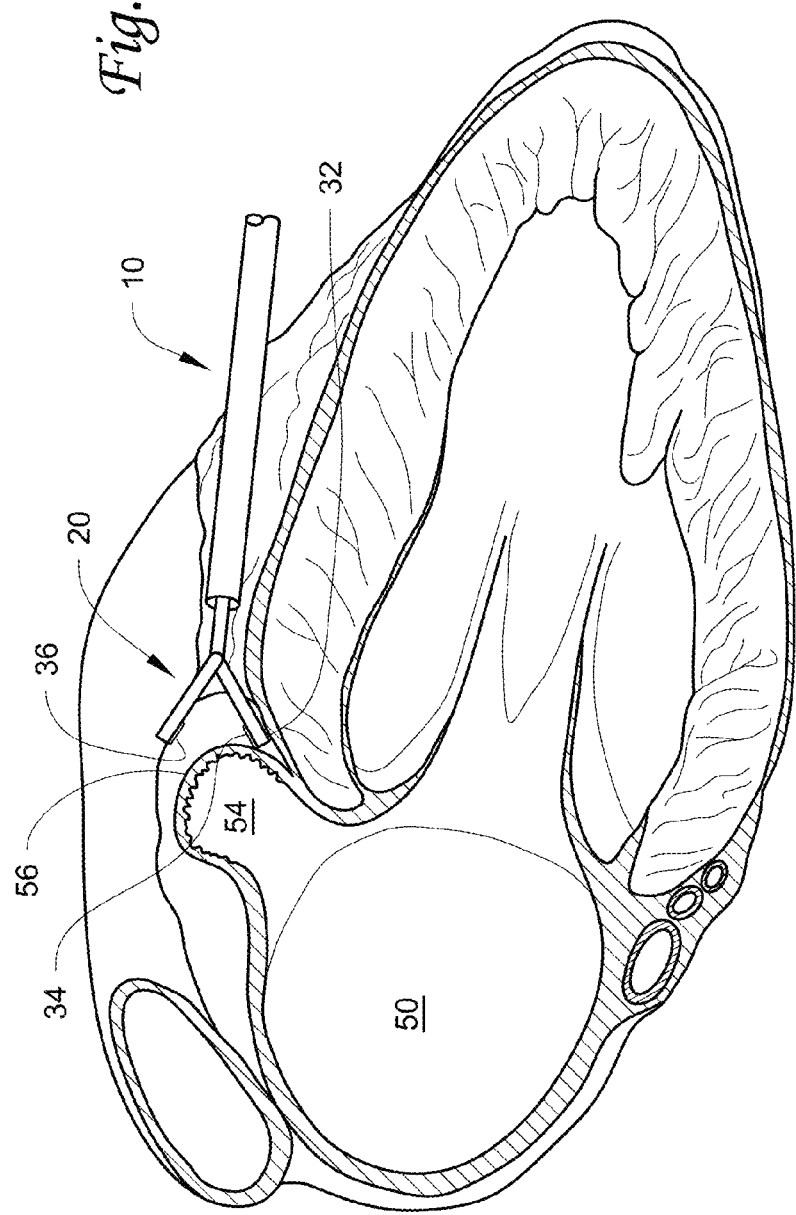
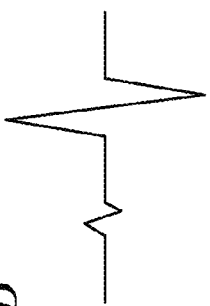
Fig. 7
Fig. 8A
Fig. 8B

ENHANCED SIGNAL NAVIGATION AND CAPTURE SYSTEMS AND METHODS

RELATED APPLICATIONS

This application is a continuation of U.S. patent application Ser. No. 13/499,431, filed on Jul. 11, 2012 (now issued U.S. Pat. No. 9,144,431), which is a U.S. National Stage Application of International Application No PCT/US2010/050835, titled ENHANCED SIGNAL NAVIGATION AND CAPTURE SYSTEMS AND METHODS, filed on 30 Sep. 2010, published in the English language on 7 Apr. 2011, as International Publication No. WO 2011/041489 A2, which claims the benefit under 35 U.S.C. §119 of U.S. Provisional Application Ser. No. 61/247,276 filed 30 Sep. 2009, entitled ENHANCED SIGNAL NAVIGATION AND CAPTURE SYSTEMS AND METHODS, all of which are incorporated herein by reference in their entireties.

Navigation and tissue capture systems and methods for navigating to and/or capturing selected tissue within the internal body of a patient using innate electrical activity of the selected tissue and/or other tissues are described herein.

Atrial fibrillation is a common cardiac rhythm disorder affecting a population of approximately 2.5 million patients in the United States alone. Atrial fibrillation results from a number of different causes and is characterized by a rapid chaotic heart beat. In addition to the risks associated with a disordered heart beat, patients with atrial fibrillation also have an increased risk of stroke. It has been estimated that approximately 75,000-90,000 atrial fibrillation patients in the United States each year suffer a stroke related to that condition. It appears that strokes in these patients result from emboli many of which may originate from the left atrial appendage. The irregular heart beat causes blood to pool in the left atrial appendage, allowing clots to accumulate over time. From time to time, a clot may dislodge from the left atrial appendage and may enter the cranial circulation causing a stroke, the coronary circulation causing a myocardial infarction, the peripheral circulation causing limb ischemia, as well as other vascular beds.

Significant efforts have been made to reduce the risk of stroke in patients suffering from atrial fibrillation. Most commonly, those patients are treated with blood thinning agents, such as Coumadin, to reduce the risk of clot formation. While such treatment can significantly reduce the risk of stroke, it also increases the risk of bleeding and for that reason is inappropriate for many atrial fibrillation patients.

As an alternative to drug therapy, minimally invasive surgical procedures for closing the left atrial appendage have been proposed. Most commonly, the left atrial appendage has been closed or removed concurrently with open surgical procedures, typically where the heart has stopped and the chest opened through the sternum. Because of the significant risk and trauma of such procedures, left atrial appendage removal occurs almost exclusively when the patient's chest is opened for other procedures, such as coronary artery bypass or valve surgery.

For that reason, alternative procedures which do not require opening of the patient's chest, i.e., a large median sternotomy, have been proposed. U.S. Pat. No. 5,306,234 to Johnson describes a thoracoscopic procedure where access to the pericardial space over the heart is achieved using a pair of intercostal penetrations (i.e., penetrations between the patients ribs) to establish both visual and surgical access. While such procedures may be performed while the heart remains beating, they still require deflation of the patient's lung and that the patient be placed under full anesthesia. Furthermore, placement of a chest tube is typically required to re-inflate the lung, often requiring a hospitalization for a couple of days.

U.S. Pat. No. 5,865,791, to Whayne et al. describes a transvascular approach for closing the left atrial appendage. Access is gained via the venous system, typically through a femoral vein, a right internal jugular vein, or a subclavian vein, where a catheter is advanced in an antegrade direction to the right atrium. The intra-atrial septum is then penetrated, and the catheter passed into the left atrium. The catheter is then positioned in the vicinity of the left atrial appendage which is then fused closed, e.g., using radiofrequency energy, other electrical energy, thermal energy, surgical adhesives, or the like. Whayne et al. further describes a thoracoscopic procedure where the pericardium is penetrated through the rib cage and a lasso placed to tie off the neck of the left atrial appendage. Other fixation means described include sutures, staples, shape memory wires, biocompatible adhesives, tissue ablation, and the like. The transvascular approach suggested by Whayne et al. is advantageous in that it avoids the need to penetrate the patient's chest but suffers from the need to penetrate the intra-atrial septum, may not provide definitive closure, requires entry into the left atrial appendage which may dislodge clot and requires injury to the endocardial surface which may promote thrombus formation. A thoracoscopic approach which is also suggested by Whayne et al. suffers from the same problems as the thoracoscopic approach suggested by Johnson.

Some improved and alternative methods and procedures for performing minimally invasive closure of the left atrial appendage are discussed in, e.g., U.S. Provisional Patent Application No. 60/826,413 filed on 21 Sep. 2006, as well as in International Publication WO 2008/036408 A2, titled DEVICES AND METHODS FOR LIGATING ANATOMICAL STRUCTURES.

These methods and procedures may preferably be capable of being performed on patients who have received only local or general anesthetic, whose hearts have not been stopped, and whose lungs are not deflated. It would be further desirable to provide methods and procedures which approach the left atrial appendage without the need to perform a thoracotomy (opening of the thorax) or the need to perform a transeptal penetration and/or perform the procedure within the left atrium or left atrial appendage. More specifically, it would be preferable to provide methods and procedures which permitted access to the pericardial space from the xiphoid region of a patient's chest.

Closure of the left atrial appendage using a percutaneous approach typically requires devices and techniques that can create a viable working space in the pericardium and provide for direct visualization of the left atrial appendage within that space. The pericardial sac is, however, very slippery, often contains fluid and is under constant motion. These factors make creating a viable working space for direct visualization difficult. Existing technologies are cumbersome (larger, non-steerable, two operator) and potentially traumatic to the cardiac arteries and veins on the epicardial surface. Unintentional trauma to a cardiac artery could cause ischemia or perforations with potentially fatal outcomes for the patient.

Direct visualization, however, requires overcoming a number of technical hurdles including creating a working space in the pericardial space to create a field of view for a videoscope or fiberscope a, removing fluids (blood) that can contaminate/obscure the lens, miniaturizing the tools to be as atraumatic as possible, identifying various anatomy within the pericardial space using only direct sight and overcoming navigation issues with pointing the field of view at the desired target while the heart is beating. Unfortunately the intravascular tools also have significant drawbacks including the risks and complications of requiring a second percutaneous intravascular access point, a transseptal puncture, causing endocardial trauma (potentially pro-thrombotic), and introducing contrast agents into the circulatory system of patients.

SUMMARY

Navigation and tissue capture systems and methods for navigation to and/or capture of selected tissue using the innate electrical activity of the selected tissue and/or other tissue are described herein. Navigation to and/or capture of selected tissue (such as, e.g., the left atrial appendage) may be enhanced by the use of a variety of systems and methods of enhancing the electrical signals obtained by various electrodes used in connection with the systems and methods.

In the context of left atrial appendage closure, the systems and methods can be used to navigate to the left atrial appendage and capture/control the appendage while a closure instrument (suture, clip, ring) is placed over the appendage and tightened down or a closure method (ablation, cryogenic procedures, stapling, etc.) is performed to close the left atrial appendage. As discussed herein, the use of innate electrical activity for navigating devices may be used in connection with other tissues and/or areas of the body.

The systems and methods described herein may preferably be used in connection with minimally invasive surgical techniques (e.g., percutaneous, laparascopic, endoscopic, etc.) in which it can be difficult to visualize the working field and/or where the available working space is limited. One example of such a situation is demonstrated by techniques that require navigation within the pericardial space to, e.g., close the left atrial appendage. The navigation and capture systems and methods rely on the detection and/or identification of innate electrical activity in the left atrial appendage or other tissue.

Although described in the context of left atrial appendage capture, the navigation and tissue capture systems and methods described herein may be used in any internal body location where detection and/or identification of innate electrical activity can be used to navigate to and/or confirm that selected tissue is captured. Other electrically active tissues in the body with which the navigation/tissue capture systems and methods could potentially be used may include, e.g., the gastrointestinal tract, central and/or peripheral nervous systems, skeletal muscle groups, etc. In any application, the systems and methods preferably take advantage of differences in and/or existence of innate electrical activity in tissues to identify tissue and/or facilitate navigation. As a result, although the embodiments discussed herein are focused on cardiac tissues, use in connection with other innately electrically active tissues is possible.

With respect to systems and devices for navigating to and capturing the left atrial appendage, the navigation and capture are preferably accomplished by monitoring cardiac electrical activity using one or more electrodes attached to one or more components of the systems as the devices are advanced through the pericardial sac. In particular, the location of system components can preferably be determined by distinguishing between the different intracardiac electrical signals (commonly referred to as an electrogram or "EGM") associated with different cardiac tissue. For example, an electrogram recorded over ventricular epicardial myocardium tissue produces a distinct EGM signal as compared with the recording over atrial epicardial myocardium tissue. As a result, a user can determine whether the electrodes on the devices are located proximate ventricular or atrial tissue based on the EGM obtained using the systems and methods described herein. Further enhancement of navigation and/or tissue capture may be obtained by systems and methods that manipulate the signals obtained from various electrodes in the system as described herein.

The systems and methods may preferably facilitate minimally invasive surgical navigation to the left atrial appendage (or other anatomy with sufficiently electrically active tissue) through a small incision or needle-stick access. The devices described herein may preferably be delivered through an introducer and sheath (that is possibly steerable or deflectable). After access to the pericardial space has been obtained, a guidewire may be placed in the pericardial space to help guide the devices further into the pericardial space. The guidewire and/or sheath may optionally include electrodes that could be used to assist with navigation to a desired location.

Each device described in connection with the systems and methods could potentially be delivered through such a sheath and into the pericardial sac. Although this technology could be used with a wide variety of surgical techniques, it may be well-suited for minimally invasive catheter based procedures. Rather than passing through the rib cage, as with some thoracoscopic techniques, the systems and methods described herein may, for example, rely on a "sub-xiphoid" approach where the percutaneous penetration is first made beneath the rib cage (preferably between the xiphoid and adjacent costal cartilage) and the device is advanced through the penetration, over the epicardial surface (in the pericardial space) to reach a location adjacent to the exterior of the left atrial appendage. Although a sub-xyphoid approach may be used, any intrapericardial access may alternatively be used regardless of method entry.

When, for example, a sub-xyphoid approach is used for intrapericardial access, the cardiac tissue encountered first is ventricular tissue which will yield an EGM indicative of ventricular cardiac tissue. As the system components are advanced towards atrial tissue (including, e.g., the left atrial appendage), the EGM signal obtained using the system should change and a unique EGM signal associated with atrial cardiac tissue should be obtained. If the system components are advanced past the left atrial appendage, the EGM signal obtained will typically have a non-atrial signature. Rather, advancement of the system components past the left atrial appendage may result in an EGM signal indicative of, e.g., the pericardium or far-field ventricular and atrial signals.

Some potentially useful systems and methods that may be used with the particular methods and systems described herein may be described in, e.g., PCT Application Serial No. US2009/38544, filed Mar. 27, 2009, entitled NAVIGATION AND TISSUE CAPTURE SYSTEMS AND METHODS.

In one aspect, embodiments of the navigation and tissue capture systems described herein include: a capture device; a capture shaft having an elongated body comprising a proximal end and a distal end, wherein the distal end of the capture shaft is attached to the capture device; a primary electrode attached to the capture device; a secondary electrode; and electrical monitoring apparatus operably connected to the primary electrode and the secondary electrode. The electrical monitoring apparatus is configured to: obtain a primary signal by monitoring cardiac electrical activity using the primary electrode; obtain a secondary signal by monitoring cardiac electrical activity using the secondary electrode; and enhance the primary signal using the secondary signal to assist in determining the location of the capture device.

In various embodiments, the secondary electrode may be a body-surface electrode locatable on a body surface and/or an electrode located on a ligation element.

In various embodiments, the systems described herein may include a delivery device having a proximal end, a distal end, and a delivery lumen having an opening proximate the distal end of the delivery device, wherein a longitudinal axis extends between the proximal end and the distal end, wherein the capture device and the capture shaft are sized for movement within the delivery lumen of the delivery device, wherein the capture device has a delivery configuration in which a distal end of the capture device is contained within the delivery lumen, wherein the capture device has an extended configuration in which the distal end of the capture device extends out of the delivery lumen proximate the distal end of the delivery device, wherein the secondary electrode is attached to the delivery device.

In various embodiments, the systems described herein may include an endocardial device, wherein the secondary electrode is attached to the endocardial device.

In various embodiments, the systems described herein may include a sheath device having a proximal end, a distal end, and a sheath lumen having an opening configured to receive the capture device, wherein a longitudinal axis extends between the proximal end and the distal end, wherein the capture shaft and capture device are sized for movement within the sheath lumen of the sheath device, wherein the system comprises a covered configuration where at a least a portion of the capture device is contained within the sheath lumen.

In various embodiments, the systems described herein may include a capture device with a first jaw and a second jaw, wherein the first jaw and the second jaw have an open configuration in which the first jaw and the second jaw are open and a closed configuration in which the first jaw and the second jaw are closed, wherein an interior surface of the first jaw is located closer to an interior surface of the second jaw when the first jaw and the second jaw are in the closed configuration than when the first jaw and the second jaw are in the open configuration, wherein the primary electrode is attached to one of the first jaw and the second jaw.

In various embodiments of the systems described herein, the electrical monitoring apparatus is configured to enhance the primary signal using the secondary signal by filtering signals from the primary signal when the secondary signal indicates ventricular activity.

In various embodiments of the systems described herein, the electrical monitoring apparatus is configured to enhance the primary signal using the secondary signal by: determining a ventricular time period based on the secondary signal; and limiting monitoring of the primary signal to time periods that fall outside of the ventricular time period.

In various embodiments of the systems described herein, the electrical monitoring apparatus is configured to enhance the primary signal using the secondary signal by: comparing the timing of the primary signal to the timing of the secondary signal; and determining what cardiac electrical activity is detected by the primary electrode based on the comparison between the timing of the primary signal and the timing of the secondary signal. The electrical monitoring apparatus may further be configured to indicate to a user that the cardiac electrical activity detected by the primary electrode is atrial cardiac electrical activity.

In various embodiments of the systems described herein, the electrical monitoring apparatus is configured to: compare the timing of the P wave component of the primary signal to the timing of the P wave component of the secondary signal; and determine what cardiac electrical activity is detected by the primary electrode based on the comparison between the timing of the P wave component of the primary signal and the timing of the P wave component of the secondary signal. The electrical monitoring apparatus may be further configured to indicate to a user that the cardiac electrical activity detected by the primary electrode is atrial cardiac electrical activity.

In various embodiments of the systems described herein, the electrical monitoring apparatus is configured to: compare the timing of the P wave component of the primary signal to the timing of the P wave component of the secondary signal; and determine what cardiac electrical activity is detected by the primary electrode based on the comparison between the timing of the P wave component of the primary signal and the timing of the P wave component of the secondary signal. The electrical monitoring apparatus may be further configured to indicate to a user that the cardiac electrical activity detected by the primary electrode is atrial cardiac electrical activity.

In various embodiments of the systems described herein, the electrical monitoring apparatus is configured to: compare the timing of the QRS complex component of the primary signal to the timing of the QRS complex component of the secondary signal; and determine what cardiac electrical activity is detected by the primary electrode based on the comparison between the timing of the QRS complex component of the primary signal and timing of the QRS complex component of the secondary signal. The electrical monitoring apparatus may be further configured to indicate to a user that the cardiac electrical activity detected by the primary electrode is atrial cardiac electrical activity.

In various embodiments of the systems described herein, the electrical monitoring apparatus is configured to: compare the slew rate of the primary signal to the slew rate of the secondary signal; and determine what cardiac electrical activity is detected by the primary electrode based on the comparison between the slew rate of the primary signal and the slew rate of the secondary signal. The electrical monitoring apparatus may be further configured to indicate to a user that the cardiac electrical activity detected by the primary electrode is atrial cardiac electrical activity.

In various embodiments of the systems described herein, the electrical monitoring apparatus is configured to: compare the relative amplitude of the primary signal to the relative amplitude of the secondary signal; and determine what cardiac electrical activity is detected by the primary electrode based on the comparison between the relative amplitude of the primary signal and the relative amplitude of the secondary signal. The electrical monitoring apparatus may be further configured to indicate to a user that the cardiac electrical activity detected by the primary electrode is atrial cardiac electrical activity.

In various embodiments of the systems described herein, the electrical monitoring apparatus is configured to: compare the area under the curve of the primary signal to the area under the curve of the secondary signal; and determine what cardiac electrical activity is detected by the primary electrode based on the comparison between the area under the curve of the primary signal and the area under the curve of the secondary signal. The electrical monitoring apparatus may be further configured to indicate to a user that the cardiac electrical activity detected by the primary electrode is atrial cardiac electrical activity.

In various embodiments of the systems described herein, the electrical monitoring apparatus is configured to: compare the relative shape of the primary signal to the relative shape of the secondary signal; and determine what cardiac electrical activity is detected by the primary electrode based on comparison between the relative shape of the primary signal and the relative shape of the secondary signal. The electrical monitoring apparatus may be further configured to indicate to a user that the cardiac electrical activity detected by the primary electrode is atrial cardiac electrical activity.

In various embodiments of the systems described herein, the electrical monitoring apparatus is configured to: compare the slope of a selected portion of the primary signal to the slope of a selected portion of the secondary signal; and determine what cardiac electrical activity is detected by the primary electrode based on comparison between the slope of the selected portion of the primary signal and the slope of the selected portion of the secondary signal. The electrical monitoring apparatus may be further configured to indicate to a user that the cardiac electrical activity detected by the primary electrode is atrial cardiac electrical activity.

In various embodiments of the systems described herein, the electrical monitoring apparatus is configured to determine the proximity of the capture device to atrial tissue based on the primary signal and the secondary signal.

In various embodiments of the systems described herein, the electrical monitoring apparatus is configured to: generate frequency domain data representative of the primary signal; generate frequency domain data representative of the secondary signal; compare the frequency domain data representative of the primary signal to the frequency domain data representative of the second signal; and determine what cardiac electrical activity is detected by the primary electrode based on comparison between the frequency domain data representative of the primary signal and the frequency domain data representative of the secondary signal. The electrical monitoring apparatus may be further configured to indicate to a user that the cardiac electrical activity detected by the primary electrode is atrial cardiac electrical activity.

In various embodiments of the systems described herein may include a capture device; a capture shaft having an elongated body with a proximal end and a distal end, wherein the distal end of the capture shaft is attached to the capture device; a shaft electrode attached to the capture shaft proximate the distal end of the capture shaft, wherein the shaft electrode is located proximally of the capture device such that the shaft electrode is located between the capture device and the proximal end of the capture shaft; a first capture device electrode attached to the capture device and a second capture device electrode attached to the capture device; and electrical monitoring apparatus operably connected to the first capture device electrode, the second capture device electrode, and the shaft electrode, wherein the electrical monitoring apparatus is configured to: obtain a far-field signal by selectively coupling the first capture device electrode and the second capture device electrode as a single conjoint electrode and monitoring electrical activity using the single conjoint electrode and the shaft electrode; and obtain a near-field signal by selectively decoupling the first capture device electrode and the second capture device electrode and monitoring electrical activity using the decoupled first capture device electrode and the second capture device electrode; compare the far-field signal to the near-field signal; and, optionally, determine what cardiac electrical activity is detected in the near-field signal based on the comparison between the far-field signal and the near-field signal.

In various embodiments of the systems described herein may include a sheath device having a proximal end, a distal end, and a sheath lumen having an opening configured to receive the capture device, wherein a longitudinal axis extends between the proximal end and the distal end, wherein the capture shaft and capture device are sized for movement within the sheath lumen of the sheath device, wherein the system has a covered configuration where at a least a portion of the capture device is contained within the sheath lumen.

In various embodiments of the systems described herein may include a capture device having a first jaw and a second jaw, wherein the first jaw and the second jaw have an open configuration in which the first jaw and the second jaw are open and a closed configuration in which the first jaw and the second jaw are closed, wherein an interior surface of the first jaw is located closer to an interior surface of the second jaw when the first jaw and the second jaw are in the closed configuration than when the first jaw and the second jaw are in the open configuration. The first capture device electrode may be attached to the first jaw and the second capture device electrode may be attached to the second jaw.

In various embodiments of the systems described herein, the electrical monitoring apparatus is configured to determine if the near-field signal comprises atrial electrical activity based on the comparison between the far-field signal and the near-field signal.

In various embodiments of the systems described herein, the electrical monitoring apparatus is configured to: obtain a shaft signal by monitoring cardiac electrical activity using the shaft electrode; and enhance the near-field signal by filtering signals from the near-field signal obtained when the shaft signal indicates ventricular activity.

In various embodiments of the systems described herein, the electrical monitoring apparatus is configured to: obtain a shaft signal by monitoring cardiac electrical activity using the shaft electrode; determine a ventricular time period based on the shaft signal; and limit monitoring of the near-field signal to time periods that fall outside of the ventricular time period.

In various embodiments of the systems described herein, the electrical monitoring apparatus is configured to compare the far-field signal to the near-field signal by comparing the timing of the near-field signal to the timing of the far-field signal.

In various embodiments of the systems described herein, the electrical monitoring apparatus is configured to compare the far-field signal to the near-field signal by comparing the timing of the P wave component of the near-field signal to the timing of the P wave component of the far-field signal.

In various embodiments of the systems described herein, the electrical monitoring apparatus is configured to compare the far-field signal to the near-field signal by comparing the timing of the QRS complex component of the near-field signal to the timing of the QRS complex component of the far-field signal.

In various embodiments of the systems described herein, the electrical monitoring apparatus is configured to compare the far-field signal to the near-field signal by comparing the slew rate of the near-field signal to the slew rate of the far-field signal.

In various embodiments of the systems described herein, the electrical monitoring apparatus is configured to compare the far-field signal to the near-field signal by comparing the relative amplitude of the near-field signal to the relative amplitude of the far-field signal.

In various embodiments of the systems described herein, the electrical monitoring apparatus is configured to compare the far-field signal to the near-field signal by comparing the area under the curve of the near-field signal to the area under the curve of the far-field signal.

In various embodiments of the systems described herein, the electrical monitoring apparatus is configured to compare the far-field signal to the near-field signal by comparing the relative shape of the near-field signal to the relative shape of the far-field signal.

In various embodiments of the systems described herein, the electrical monitoring apparatus is configured to compare the far-field signal to the near-field signal by comparing the slope of a selected portion of the primary signal to the slope of a selected portion of the secondary signal.

In various embodiments of the systems described herein, the electrical monitoring apparatus is configured to determine the proximity of the capture device to atrial tissue based on the comparison between the near-field signal and the far-field signal.

In various embodiments of the systems described herein, the electrical monitoring apparatus is configured to compare the far-field signal to the near-field signal by: generate frequency domain data representative of the near-field signal; generate frequency domain data representative of the far-field signal; and compare the frequency domain data representative of the near-field signal to the frequency domain data representative of the far-field signal.

In various embodiments of the systems described herein, the electrical monitoring apparatus is configured to indicate to a user that the cardiac electrical activity detected in the near-field signal comprises atrial cardiac electrical activity.

In various embodiments, the systems described herein include a capture device; a capture shaft comprising an elongated body comprising a proximal end and a distal end, wherein the distal end of the capture shaft is attached to the capture device; a primary electrode attached to the capture device; and electrical monitoring apparatus operably connected to the primary electrode, wherein the electrical monitoring apparatus is configured to: obtain a baseline signal by monitoring electrical activity of a selected tissue using the primary electrode; store the baseline signal; obtain a primary signal by monitoring electrical activity using the primary electrode; compare the primary signal to the stored baseline signal; and determine what cardiac electrical activity is detected by the primary electrode based on the comparison between the primary signal to the baseline signal.

In various embodiments, the systems described herein may include a sheath device comprising a proximal end, a distal end, and a sheath lumen comprising an opening configured to receive the capture device, wherein a longitudinal axis extends between the proximal end and the distal end, wherein the capture shaft and capture device are sized for movement within the sheath lumen of the sheath device, wherein the system comprises a covered configuration where at a least a portion of the capture device is contained within the sheath lumen.

In various embodiments of the systems described herein, the capture device comprises a first jaw and a second jaw, wherein the first jaw and the second jaw comprise an open configuration in which the first jaw and the second jaw are open and a closed configuration in which the first jaw and the second jaw are closed, wherein an interior surface of the first jaw is located closer to an interior surface of the second jaw when the first jaw and the second jaw are in the closed configuration than when the first jaw and the second jaw are in the open configuration, wherein the primary electrode is attached to one of the first jaw and the second jaw.

In various embodiments of the systems described herein, the selected tissue comprises atrial tissue.

In various embodiments of the systems described herein, the electrical monitoring apparatus is configured to compare the primary signal to the stored baseline signal by comparing the timing of the primary signal to the timing of the baseline signal.

In various embodiments of the systems described herein, the electrical monitoring apparatus is configured to compare the primary signal to the stored baseline signal by comparing the timing of the P wave component of the primary signal to the timing of the P wave component of the baseline signal.

In various embodiments of the systems described herein, the electrical monitoring apparatus is configured to compare the primary signal to the stored baseline signal by comparing the timing of the QRS complex component of the primary signal to the timing of the QRS complex component of the baseline signal.

In various embodiments of the systems described herein, the electrical monitoring apparatus is configured to compare the primary signal to the stored baseline signal by comparing the slew rate of the primary signal to the slew rate of the baseline signal.

In various embodiments of the systems described herein, the electrical monitoring apparatus is configured to compare the primary signal to the stored baseline signal by comparing the relative amplitude of the primary signal to the relative amplitude of the baseline signal.

In various embodiments of the systems described herein, the electrical monitoring apparatus is configured to compare the primary signal to the stored baseline signal by comparing the area under the curve of the primary signal to the area under the curve of the baseline signal.

In various embodiments of the systems described herein, the electrical monitoring apparatus is configured to compare the primary signal to the stored baseline signal by comparing the relative shape of the primary signal to the relative shape of the baseline signal.

In various embodiments of the systems described herein, the electrical monitoring apparatus is configured to compare the primary signal to the stored baseline signal by comparing the slope of a selected portion of the primary signal to the slope of a selected portion of the baseline signal.

In various embodiments of the systems described herein, the electrical monitoring apparatus is configured to determine the proximity of the capture device to atrial tissue based on the comparison between the primary signal and the baseline signal.

In various embodiments of the systems described herein, the electrical monitoring apparatus is configured to compare the primary signal to the stored baseline signal by: generating frequency domain data representative of the primary signal; generating frequency domain data representative of the baseline signal; and comparing the frequency domain data representative of the primary signal to the frequency domain data representative of the second signal.

In various embodiments of the systems described herein, the electrical monitoring apparatus is configured to indicate to a user that the cardiac electrical activity detected in the primary signal comprises atrial cardiac electrical activity.

The navigation to and capture of the left atrial appendage may be used to provide stability for subsequent procedures. The left atrial appendage may be stabilized and/or captured for any number of procedures including ablation, drug delivery, isolation, ligation, diagnostic mapping, etc. The systems and methods described herein may help navigate to and locate the left atrial appendage through minimally invasive approaches.

Although the systems and methods described herein may use EGM signals for navigation and tissue capture with respect to the left atrial appendage, other navigation techniques may be used in combination with EGM-based navigation, such as, e.g., fluoroscopy, echocardiography, MRI, CT scanning, ultrasonic imaging, direct visualization (using, e.g., fiberoptic devices), etc.

For example, the methods described herein may include navigating a device to an anatomical structure by delivering a device into the anatomical area; injecting image enhancement liquid into the anatomical area; and identifying the location of the device and/or the locations of anatomical structures (e.g., the left atrial appendage) using fluoroscopic or other imaging techniques that may be enhanced by injection of the image enhancement liquid.

In another aspect, a navigation and tissue capture system may be provided that includes a capture device having a first jaw and a second jaw, wherein the first jaw and the second jaw have an open configuration in which the first jaw and the second jaw are open and a closed configuration in which the first jaw and the second jaw are closed, wherein an interior surface of the first jaw is located closer to an interior surface of the second jaw when the first jaw and the second jaw are in the closed configuration than when the first jaw and the second jaw are in the open configuration; a capture shaft having an elongated body with a proximal end and a distal end, wherein the distal end of the capture shaft is attached to the capture device; a capture shaft electrode attached to the capture shaft proximate the distal end of the capture shaft, wherein the capture shaft electrode is located proximal of the capture device; a capture shaft electrode conductor extending from the capture shaft electrode towards the proximal end of the capture shaft, wherein the capture shaft conductor includes an electrical monitoring apparatus connector; a first electrode attached to the capture device; and a first electrode lead extending from the first electrode towards the proximal end of the capture shaft, wherein the first electrode lead has an electrical monitoring apparatus connector.

In some embodiments, the navigation and tissue capture systems described herein may include a delivery device having a proximal end, a distal end, and a capture lumen that includes an opening proximate the distal end of the delivery device, wherein a longitudinal axis extends between the proximal end and the distal end; wherein the capture device and the capture shaft are sized for movement within the capture lumen of the delivery device; and wherein the capture device has a delivery configuration in which a distal end of the capture device is contained within the capture lumen, and wherein the capture device has an extended configuration in which the distal end of the capture device extends out of the capture lumen proximate the distal end of the delivery device. The systems may also include a delivery device electrode attached to an exterior of the delivery device proximate the distal end of the capture device; and a delivery device electrode lead extending from the delivery device electrode towards the proximal end of the delivery device, wherein the delivery device electrode lead has an electrical monitoring apparatus connector; etc.

In some embodiments of systems described herein that include a first and second electrode, one or more of the following features may be provided: the first electrode may be exposed on an interior surface of the first jaw of the capture device and the second electrode may be exposed on an interior surface of the second jaw of the capture device; the first electrode may be the only electrode on an interior surface of the first jaw and the second electrode may be the only electrode on an interior surface of the second jaw; the first electrode may occupy about one quarter or more of the interior surface of the first jaw, and the second electrode may occupy about one quarter or more of the interior surface of the second jaw; the first electrode may be positioned on the first jaw and the second electrode may be positioned on the second jaw such that closure of the first jaw and the second jaw in the absence of tissue between the first jaw and the second jaw places the first electrode and the second electrode in contact with each other; etc.

In another aspect, a method of navigating to selected internal body tissue is described that includes delivering the capture device of a navigation and tissue capture system described herein to an internal body location; monitoring innate electrical activity in tissue proximate the internal body location using the capture shaft electrode; capturing tissue using the capture device; and monitoring innate electrical activity in tissue captured by the capture device. In some embodiments, the internal body location may be the pericardial space and the captured tissue may include the left atrial appendage.

In another aspect, a navigation and tissue capture system is described that includes a delivery device having a proximal end, a distal end, and a capture lumen having an opening proximate the distal end of the delivery device, wherein a longitudinal axis extends between the proximal end and the distal end; a capture device sized for movement within the capture lumen of the delivery device, wherein the capture device has a delivery configuration in which a distal end of the capture device is contained within the capture lumen, and wherein the capture device has an extended configuration in which the distal end of the capture device extends out of the capture lumen proximate the distal end of the delivery device; a capture shaft having a distal end operably attached to the capture device, the capture shaft extending through the capture lumen from a proximal end of the capture lumen to the capture device; a capture shaft electrode attached to the capture shaft proximate the distal end of the capture shaft, wherein the capture shaft electrode is located proximal of the capture device; a capture shaft electrode conductor extending from the capture shaft electrode towards the proximal end of the capture shaft, wherein the capture shaft conductor includes a connector adapted for connection to an EGM monitoring apparatus; a primary capture electrode attached to the capture device; and a primary capture electrode lead extending from the primary capture electrode towards the proximal end of the delivery device, wherein the primary capture electrode lead includes a connector adapted for connection to an EGM monitoring apparatus.

In another aspect, a navigation and tissue capture system may be provided that includes a delivery device having a proximal end, a distal end, and a capture lumen having an opening proximate the distal end of the delivery device, wherein a longitudinal axis extends between the proximal end and the distal end; a capture device having a first jaw and a second jaw, wherein the first jaw and the second jaw have an open configuration in which the first jaw and the second jaw are open and a closed configuration in which the first jaw and the second jaw are closed; the capture device sized for movement within the capture lumen of the delivery device, wherein the capture device has a delivery configuration in which a distal end of the capture device is contained within the capture lumen, and wherein the capture device has an extended configuration in which the distal end of the capture device extends out of the capture lumen proximate the distal end of the delivery device; a capture shaft having a distal end operably attached to the capture device, the capture shaft extending through the capture lumen from a proximal end of the capture lumen to the capture device; a capture shaft electrode attached to the capture shaft proximate the distal end of the capture shaft, wherein the capture shaft electrode is located proximal of the capture device; a capture shaft electrode conductor extending from the capture shaft electrode towards the proximal end of the capture shaft, wherein the capture shaft conductor includes an EGM monitoring apparatus connector; a first electrode exposed on an interior surface of the first jaw of the capture device; and a first electrode lead extending from the first electrode towards the proximal end of the delivery device, wherein the first electrode lead includes an EGM monitoring apparatus connector.

In various embodiments, the system described above may include one or more of the following features: a second electrode exposed on an interior surface of the second jaw of the capture device and a second electrode lead extending from the second electrode towards the proximal end of the delivery device, wherein the second electrode lead includes an EGM monitoring apparatus connector; the first electrode and the second electrode may be arranged such that closure of the first jaw and the second jaw in the absence of tissue between the first jaw and the second jaw causes the first electrode and the second electrode to contact each other; an external electrode may be located on an external surface of the first jaw; and an external electrode lead may extend from the external electrode towards the proximal end of the delivery device, wherein the external electrode lead includes an EGM monitoring apparatus connector; the first electrode may occupy about one quarter or more of the interior surface of the first jaw; the capture shaft may include an actuator extending through the capture shaft to the capture device, wherein movement of the actuator within the capture shaft proximally and distally moves the first jaw and the second jaw of the capture device between the closed configuration and the open configuration; etc.

In another aspect, a navigation and tissue capture system may be provided that includes a delivery device having a proximal end, a distal end, and a capture lumen with an opening proximate the distal end of the delivery device, wherein a longitudinal axis extends between the proximal end and the distal end; a capture device having a first jaw and a second jaw, wherein the first jaw and the second jaw have an open configuration in which the first jaw and the second jaw are open and a closed configuration in which the first jaw and the second jaw are closed; the capture device sized for movement within the capture lumen of the delivery device, wherein the capture device has a delivery configuration in which a distal end of the capture device is contained within the capture lumen, and wherein the capture device has an extended configuration in which the distal end of the capture device extends out of the capture lumen proximate the distal end of the delivery device; a capture shaft having a distal end operably attached to the capture device, the capture shaft extending through the capture lumen from a proximal end of the capture lumen to the capture device; a capture shaft electrode attached to the capture shaft proximate the distal end of the capture shaft, wherein the capture shaft electrode is located proximal of the capture device; a capture shaft electrode conductor extending from the capture shaft electrode towards the proximal end of the capture shaft, wherein the capture shaft conductor includes an EGM monitoring apparatus connector; a first electrode and a second electrode, wherein the first electrode and the second electrode are exposed on an interior surface of the first jaw of the capture device; a first electrode lead extending from the first electrode towards the proximal end of the delivery device, wherein the first electrode lead includes an EGM monitoring apparatus connector; and a second electrode lead extending from the second electrode towards the proximal end of the delivery device, wherein the second electrode lead includes an EGM monitoring apparatus connector.

In various embodiments, the system described above may include one or more of the following features: the interior surface of the second jaw may include an electrically conductive surface such that closure of the first jaw and the second jaw in the absence of tissue between the first jaw and the second jaw places the first electrode and the second electrode in electrical communication with each other through the electrically conductive surface; an external electrode may be located on an external surface of the first jaw; and an external electrode lead may extend from the external electrode towards the proximal end of the delivery device, wherein the external electrode lead includes an EGM monitoring apparatus connector; the capture shaft may include an actuator extending through the capture shaft to the capture device, wherein movement of the actuator within the capture shaft proximally and distally moves the first jaw and the second jaw of the capture device between the closed configuration and the open configuration; etc.

In another aspect, a navigation and tissue capture system may be provided that includes a capture shaft having a proximal end and a distal end, wherein the capture shaft defines a longitudinal axis extending from the proximal end to the distal end;

a capture device attached to the distal end of the capture shaft, the capture device having a first jaw and a second jaw, wherein the capture device has a closed configuration in which the first jaw and the second jaw are closed and an open configuration in which the first jaw and the second jaw are open; and wherein at least one of the first jaw and the second jaw rotate about an axis oriented generally transverse to the longitudinal axis of the capture shaft when the first jaw and the second jaw move between the open configuration and the closed configuration; a capture shaft electrode attached to the capture shaft proximate the distal end of the capture shaft, wherein the capture shaft electrode is located proximal of the capture device; a capture shaft electrode conductor extending from the capture shaft electrode towards the proximal end of the capture shaft, wherein the capture shaft conductor includes an EGM monitoring apparatus connector; a first electrode exposed on an interior surface of the first jaw of the capture device; and a first electrode lead extending from the first electrode towards the proximal end of the delivery device, wherein the first electrode lead includes an EGM monitoring apparatus connector.

In various embodiments, the system described above may include one or more of the following features: a second electrode exposed on an interior surface of the second jaw of the capture device and a second electrode lead extending from the second electrode towards the proximal end of the delivery device, wherein the second electrode lead includes an EGM monitoring apparatus connector; the first electrode may be positioned on the first jaw and the second electrode may be positioned on the second jaw such that closure of the first jaw and the second jaw in the absence of tissue between the first jaw and the second jaw places the first electrode and the second electrode in contact with each other; an external electrode may be located on an external surface of at least one of the first jaw and the second jaw, and an external electrode lead may extend from the external electrode towards the proximal end of the delivery device, wherein the external electrode lead includes an EGM monitoring apparatus connector; the first electrode may occupy about one quarter or more of the interior surface of the first jaw; the capture shaft may include an actuator extending through the capture shaft to the capture device, wherein movement of the actuator within the capture shaft proximally and distally moves the capture device between the closed configuration and the open configuration; etc.

In another aspect, a navigation and tissue capture system may be provided that includes a capture shaft having a proximal end and a distal end, wherein the capture shaft defines a longitudinal axis extending from the proximal end to the distal end; a capture device attached to the distal end of the capture shaft, the capture device having a first jaw and a second jaw, wherein the capture device has a closed configuration in which the first jaw and the second jaw are closed and an open configuration in which the first jaw and the second jaw are open; and wherein at least one of the first jaw and the second jaw rotate about an axis oriented generally transverse to the longitudinal axis of the capture shaft when the first jaw and the second jaw move between the open configuration and the closed configuration; an external electrode located on an external surface of at least one of the first jaw and the second jaw; and an external electrode lead extending from the external electrode towards the proximal end of the delivery device, wherein the external electrode lead includes an EGM monitoring apparatus connector; a first electrode exposed on an interior surface of the first jaw of the capture device; and a first electrode lead extending from the first electrode towards the proximal end of the delivery device, wherein the first electrode lead includes an EGM monitoring apparatus connector.

In various embodiments, the systems described above may include one or more of the following features: a second electrode exposed on an interior surface of the second jaw of the capture device and a second electrode lead extending from the second electrode towards the proximal end of the delivery device, wherein the second electrode lead includes an EGM monitoring apparatus connector; the first electrode positioned on the first jaw and the second electrode positioned on the second jaw such that closure of the first jaw and the second jaw in the absence of tissue between the first jaw and the second jaw places the first electrode and the second electrode in contact with each other; the first electrode may occupy about one quarter or more of the interior surface of the first jaw; the capture shaft having an actuator extending through the capture shaft to the capture device, wherein movement of the actuator within the capture shaft proximally and distally moves the capture device between the closed configuration and the open configuration; etc.

In another aspect, a navigation and tissue capture system may be provided that includes a capture shaft having a proximal end and a distal end, wherein the capture shaft defines a longitudinal axis extending from the proximal end to the distal end; a capture device attached to the distal end of the capture shaft, the capture device having a first jaw and a second jaw, wherein the capture device has a closed configuration in which the first jaw and the second jaw are closed and an open configuration in which the first jaw and the second jaw are open, wherein an interior surface of the first jaw is located closer to an interior surface of the second jaw when the first jaw and the second jaw are in the closed configuration than when the first jaw and the second jaw are in the open configuration; an electrode exposed on an interior surface of the first jaw of the capture device; and a first electrode lead extending from the first electrode towards the proximal end of the delivery device, wherein the first electrode lead includes an EGM monitoring apparatus connector; wherein the interior surface of the second jaw does not contain any electrodes capable of sensing innate electrical activity of tissue located between the first jaw and the second jaw.

In another aspect, a navigation and tissue capture system may be provided that includes a capture shaft having a proximal end and a distal end, wherein the capture shaft defines a longitudinal axis extending from the proximal end to the distal end; a capture device attached to the distal end of the capture shaft, the capture device having a first jaw and a second jaw, wherein the capture device has a closed configuration in which the first jaw and the second jaw are closed and an open configuration in which the first jaw and the second jaw are open, wherein an interior surface of the first jaw is located closer to an interior surface of the second jaw when the first jaw and the second jaw are in the closed configuration than when the first jaw and the second jaw are in the open configuration; a first electrode exposed on an interior surface of the first jaw of the capture device, wherein the first electrode occupies about one quarter or more of the interior surface of the first jaw; and a first electrode lead extending from the first electrode towards the proximal end of the delivery device, wherein the first electrode lead includes an EGM monitoring apparatus connector.

In another aspect, a navigation and tissue capture system may be provided that includes a delivery device having a proximal end, a distal end, and a capture lumen having an opening proximate the distal end of the delivery device, wherein a longitudinal axis extends between the proximal end and the distal end; a delivery device electrode attached to the delivery device proximate the distal end of the delivery device; a delivery device electrode lead extending from the delivery device electrode towards the proximal end of the delivery device, wherein the delivery device electrode lead includes a connector adapted for connection to an EGM monitoring apparatus; a capture device sized for movement within the capture lumen of the delivery device, wherein the capture device has a delivery configuration in which a distal end of the capture device is contained within the capture lumen, and wherein the capture device has an extended configuration in which the distal end of the capture device extends out of the capture lumen proximate the distal end of the delivery device; a primary capture electrode attached to the capture device; and a primary capture electrode lead extending from the primary capture electrode towards the proximal end of the delivery device, wherein the primary capture electrode lead includes a connector adapted for connection to an EGM monitoring apparatus.

In various embodiments, the system described above may include one or more of the following features: the primary capture electrode is located within the capture lumen when the capture device is in the delivery configuration, and wherein the primary capture electrode is located outside of the capture lumen when the capture device is in the extended configuration; the capture device includes a grasping apparatus having a first jaw and a second jaw, wherein closure of the grasping apparatus includes movement of the first jaw and the second jaw towards each other to capture tissue between the first jaw and the second jaw; the primary capture electrode is attached to the first jaw; the capture device includes an auxiliary capture electrode attached to the second jaw; the primary capture electrode and the auxiliary capture electrode are arranged such that closure of the grasping apparatus in the absence of tissue between the first jaw and the second jaw causes the primary electrode and the auxiliary electrode to contact each other; the first jaw and the second jaw are arranged opposite from each other, and wherein the first jaw and the second jaw both have an internal surface facing the opposing jaw and an external surface facing away from the opposing jaw, and further wherein the primary capture electrode is located on one of the external surfaces of the first jaw and the second jaw; a first jaw electrode located on the internal surface of the first jaw and a second jaw electrode located on the internal surface of the second jaw, and further wherein the first jaw electrode and the second jaw electrode are arranged such that closure of the grasping apparatus in the absence of tissue between the first jaw and the second jaw causes the first jaw electrode and the second jaw electrode to contact each other; the capture device includes a cage; the delivery device includes a ligation lumen having a ligation opening proximate the distal end of the delivery device; etc.

In another aspect, a navigation and tissue capture system may be provided that includes a delivery device comprising a proximal end, a distal end, and a capture lumen comprising an opening proximate the distal end of the delivery device, wherein a longitudinal axis extends between the proximal end and the distal end; a capture device sized for movement within the capture lumen of the delivery device, wherein the capture device includes a delivery configuration in which a distal end of the capture device is contained within the capture lumen, and wherein the capture device has an extended configuration in which the distal end of the capture device extends out of the capture lumen proximate the distal end of the delivery device; a primary capture electrode attached to the capture device; and a primary capture electrode lead extending from the primary capture electrode towards the proximal end of the delivery device, wherein the primary capture electrode lead includes a connector adapted for connection to an EGM monitoring apparatus.

In various embodiments, the system described above may include one or more of the following features: the primary capture electrode is located within the capture lumen when the capture device is in the delivery configuration, and wherein the primary capture electrode is located outside of the capture lumen when the capture device is in the extended configuration; the capture device includes a grasping apparatus having a first jaw and a second jaw, wherein closure of the grasping apparatus includes movement of the first jaw and the second jaw towards each other to capture tissue between the first jaw and the second jaw; the primary capture electrode is attached to the first jaw; the capture device includes an auxiliary capture electrode attached to the second jaw; the primary capture electrode and the auxiliary capture electrode are arranged such that closure of the grasping apparatus in the absence of tissue between the first jaw and the second jaw causes the primary electrode and the auxiliary electrode to contact each other; the first jaw and the second jaw are arranged opposite from each other, and wherein the first jaw and the second jaw both have an internal surface facing the opposing jaw and an external surface facing away from the opposing jaw, and further wherein the primary capture electrode is located on one of the external surfaces of the first jaw and the second jaw; a first jaw electrode located on the internal surface of the first jaw and a second jaw electrode located on the internal surface of the second jaw, and further wherein the first jaw electrode and the second jaw electrode are arranged such that closure of the grasping apparatus in the absence of tissue between the first jaw and the second jaw causes the first jaw electrode and the second jaw electrode to contact each other; the capture device includes a cage; the delivery device includes a ligation lumen having a ligation opening proximate the distal end of the delivery device; etc.

Any of the navigation and tissue capture systems described herein may include an EGM monitor device capable of displaying EGM signals obtained from one or more electrodes provided in the systems.

Any of the navigation and tissue capture systems described herein may include a delivery device and/or a capture shaft that includes at least one image enhancement liquid injection lumen having an injection opening proximate the distal end of the delivery device and/or the capture shaft.

In another aspect, a kit may be provided that includes any of the navigation and tissue capture systems described herein along with an image enhancement liquid injection device. The kit may further include a container of image enhancement liquid.

In another aspect, a method of navigating a device to the left atrial appendage may be provided that includes delivering a device into the pericardial sac; detecting an EGM signal within the pericardial sac using one or more electrodes on the device; identifying the location of the device relative to the left atrial appendage by determining if the EGM signal is associated with atrial epicardial tissue; optionally confirming capture of the left atrial appendage by a capture device by determining if an EGM signal obtained from tissue captured by the capture device is associated with tissue of the left atrial appendage; and optionally confirming capture of atrial tissue by electrically stimulating the atrial tissue and confirming that the tissue is being paced.

In various embodiments, the methods described above may include injecting image enhancement liquid within the pericardial sac using one or more image enhancement liquid injector lumens on the device; and identifying the location of the device relative to the left atrial appendage using an imaging technique.

In another aspect, a navigation and tissue capture system is provided that includes a delivery device having a proximal end, a distal end, and a capture lumen that includes an opening proximate the distal end of the delivery device, wherein a longitudinal axis extends between the proximal end and the distal end; a delivery device electrode attached to the delivery device proximate the distal end of the delivery device; a delivery device electrode lead extending from the delivery device electrode towards the proximal end of the delivery device, wherein the delivery device electrode lead comprises a connector adapted for connection to an EGM monitoring apparatus; a capture device sized for movement within the capture lumen of the delivery device, wherein the capture device has a delivery configuration in which a distal end of the capture device is contained within the capture lumen, and wherein the capture device has an extended configuration in which the distal end of the capture device extends out of the capture lumen proximate the distal end of the delivery device; a primary capture electrode attached to the capture device; and a primary capture electrode lead extending from the primary capture electrode towards the proximal end of the delivery device, wherein the primary capture electrode lead includes a connector adapted for connection to an EGM monitoring apparatus.

In various aspects, the systems may include one or more of the following features. The primary capture electrode may be located within the capture lumen when the capture device is in the delivery configuration, and the primary capture electrode may be located outside of the capture lumen when the capture device is in the extended configuration. The capture device may be a grasping apparatus that includes a first jaw and a second jaw, wherein closure of the grasping apparatus includes movement of the first jaw and the second jaw towards each other to capture tissue between the first jaw and the second jaw; the primary capture electrode may be attached to the first jaw; the capture device may include an auxiliary capture electrode attached to the second jaw. The primary capture electrode and the auxiliary capture electrode may be arranged such that closure of the grasping apparatus in the absence of tissue between the first jaw and the second jaw causes the primary electrode and the auxiliary electrode to contact each other. The first jaw and the second jaw may be arranged opposite from each other, and wherein the first jaw and the second jaw both include an internal surface facing the opposing jaw and an external surface facing away from the opposing jaw, and further wherein the primary capture electrode is located on one of the external surfaces of the first jaw and the second jaw. A first jaw electrode may be located on the internal surface of the first jaw and a second jaw electrode may be located on the internal surface of the second jaw, wherein the first jaw electrode and the second jaw electrode may be arranged such that closure of the grasping apparatus in the absence of tissue between the first jaw and the second jaw causes the first jaw electrode and the second jaw electrode to contact each other. The system may include a return and/or tracking electrode adapted for attachment to the skin of a patient. The capture device may include a barbed hook, a tissue screw; a cryogenic device; a cage, a lasso, a suction device, adhesive, RF energy, etc. The delivery device may include a ligation lumen having a ligation opening proximate the distal end of the delivery device. The system may include an EGM monitor device capable of displaying EGM signals obtained from one or more electrodes of the tissue capture system.

In another aspect, a navigation and tissue capture system may be provided that includes a delivery device having a proximal end, a distal end, and a capture lumen that includes an opening proximate the distal end of the delivery device, wherein a longitudinal axis extends between the proximal end and the distal end; a capture device sized for movement within the capture lumen of the delivery device, wherein the capture device has a delivery configuration in which a distal end of the capture device is contained within the capture lumen, and wherein the capture device has an extended configuration in which the distal end of the capture device extends out of the capture lumen proximate the distal end of the delivery device; a primary capture electrode attached to the capture device; and a primary capture electrode lead extending from the primary capture electrode towards the proximal end of the delivery device, wherein the primary capture electrode lead includes a connector adapted for connection to an EGM monitoring apparatus.

In various aspects, the navigation and tissue capture system described above may include one or more of the following features. The primary capture electrode may be located within the capture lumen when the capture device is in the delivery configuration, and the primary capture electrode may be located outside of the capture lumen when the capture device is in the extended configuration. The capture device may include a grasping apparatus having a first jaw and a second jaw, wherein closure of the grasping apparatus includes movement of the first jaw and the second jaw towards each other to capture tissue between the first jaw and the second jaw. The primary capture electrode may be attached to the first jaw. The capture device may include an auxiliary capture electrode attached to the second jaw. The primary capture electrode and the auxiliary capture electrode may be arranged such that closure of the grasping apparatus in the absence of tissue between the first jaw and the second jaw causes the primary electrode and the auxiliary electrode to contact each other. The first jaw and the second jaw are arranged opposite from each other, and the first jaw and the second jaw both include an internal surface facing the opposing jaw and an external surface facing away from the opposing jaw, and further wherein the primary capture electrode is located on one of the external surfaces of the first jaw and the second jaw. A first jaw electrode may be located on the internal surface of the first jaw and a second jaw electrode may be located on the internal surface of the second jaw, and further wherein the first jaw electrode and the second jaw electrode may be arranged such that closure of the grasping apparatus in the absence of tissue between the first jaw and the second jaw causes the first jaw electrode and the second jaw electrode to contact each other. The system may include a return electrode adapted for attachment to the skin of a patient. The capture device may include a barbed hook, a tissue screw; a cryogenic device; a cage, a lasso, a suction device, adhesive, etc. The delivery device may include a ligation lumen comprising a ligation opening proximate the distal end of the delivery device. The system may include an EGM monitor device capable of displaying EGM signals obtained from one or more electrodes of the tissue capture system. The system may include a device operable for delivering image enhancement liquid to the distal end of the device to determine the location of the device and/or the locations of anatomical structures (e.g., the left atrial appendage) using fluoroscopic and/or other imaging techniques.

In another aspect, a method is provided that may include navigating a device to the left atrial appendage by delivering a device into the pericardial sac; detecting an EGM signal within the pericardial sac using one or more electrodes on the device; identifying the location of the device relative to the left atrial appendage by determining if the EGM signal is associated with atrial epicardial tissue; optionally confirming capture of the left atrial appendage by a capture device by determining if an EGM signal obtained from tissue captured by the capture device is associated with tissue of the left atrial appendage.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, an electrode may be used to refer to one, two, three or more electrodes.

The term "and/or" means one or all of the listed elements or a combination of any two or more of the listed elements.

The above summary is not intended to describe each embodiment or every implementation of the navigation and tissue capture systems described herein. Rather, a more complete understanding of the navigation and tissue capture systems described herein will become apparent and appreciated by reference to the following Detailed Description of Exemplary Embodiments and claims in view of the accompanying figures of the drawing.

BRIEF DESCRIPTION OF THE VIEWS OF THE DRAWING

FIG. 7 is a cross-sectional view of the human heart showing the left side anatomy, with the capture device of FIG. 1 capturing the left atrial appendage.

FIG. 8A depicts a representative electrogram (EGM) across the interior electrodes on the jaws of the capture device of FIG. 7.

FIG. 8B depicts a representative electrogram (EGM) as detected by the external electrode while grasping the left atrial appendage tissue.

DETAILED DESCRIPTION OF EXEMPLARY EMBODIMENTS

Figure 1:
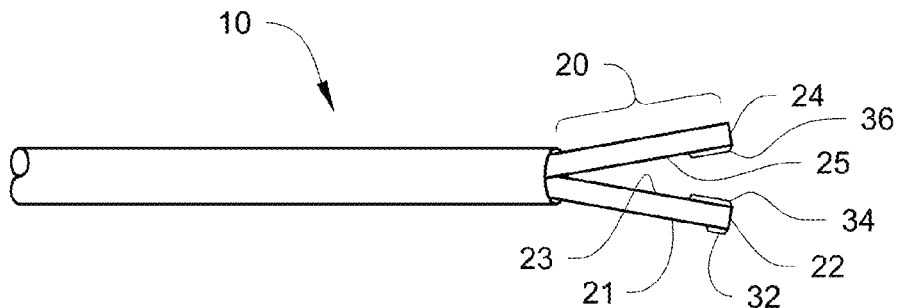
FIG. 1 depicts one exemplary embodiment of a delivery device with a capture device extending out of a delivery lumen in the delivery device.

In the following detailed description of exemplary embodiments, reference is made to the accompanying figures of the drawing which form a part hereof, and in which are shown, by way of illustration, specific embodiments in which the systems and/or methods may be practiced. It is to be understood that other embodiments may be utilized and structural changes may be made without departing from the scope of the present invention.

One exemplary embodiment of a tissue capture system including a delivery device 10 and a capture device 20 is depicted in FIG. 1. The delivery device 10 may be provided in the form of, e.g., a sheath (that may or may not be provided with an introducer and/or dilator as is known), catheter, or other elongate structure. The delivery device 10 may or may not be flexible. The delivery device 10 itself may preferably be steerable or deflectable. The delivery device 10 is also optional, i.e., the navigation and tissue capture systems described herein may not include a delivery sheath.

The proximal end of the capture device 20 may preferably include a user interface that allows an operator to deploy and retract the capture device 20 from within the delivery device 10, a mechanism to actuate the capture device 20, and optionally a mechanism to steer the capture device separately from the delivery device 10.

In the depicted embodiment, the delivery device 10 includes a lumen through which the capture device 20 can be advanced or retracted to assist with delivery of the capture device 20 to a selected internal body location. Although the delivery device 10 may include as few as one lumen as depicted in FIG. 1, it may include two or more lumens that may be used to provide pathways to deliver other devices, provide visual access, fluid access, etc. The capture device 20 may preferably extend out of the proximal end of the delivery device 10 such that it can be controlled by a user also operating the delivery device 10 as is conventional in the use of minimally invasive surgical devices.

The capture device 20 is depicted in FIG. 1 in an extended configuration in which the distal end of the capture device 20 extends out of the lumen in the delivery device 10 proximate the distal end of the delivery device 10. Although not depicted, the capture device 20 is preferably movable within the lumen of the delivery device 10 such that the capture device 20 can be moved between the extended position depicted in FIG. 1 and a delivery configuration in which a distal end of the capture device 20 is contained within the lumen of the delivery device 10. A potential benefit of having the capture device 20 retracted into the delivery device 10 during delivery is a reduction in the likelihood of trauma to the epicardial surface at the delivery site and on the path to the delivery site (e.g., a left atrial appendage).

The capture device 20 depicted in FIG. 1 is in the form of a grasping apparatus that includes two jaws 22 and 24. The jaws 22 and 24 can preferably be moved between on open position adapted to allow tissue to enter the space between the open jaws 22 and 24 and a closed position in the jaws 22 and 24 are moved towards each other to capture tissue that can be grasped between the jaws 22 and 24. The jaws of the grasping apparatus can be actuated by any suitable technique (e.g., mechanical linkage, memory material that is closed when drawn into the delivery device, electrical activation, hydraulically, pneumatically, magnetically, etc.). Although the grasping apparatus of the capture device 20 includes two jaws, it should be understood that other grasping apparatus may be provided that include three or more jaws (and that other apparatus for capturing tissue may be used in place of, or in addition to, apparatus that use jaws).

Also, although the exemplary systems and methods are described in connection with a grasping apparatus as a tissue capture device, it should be understood that the systems and methods may be used in connection with a wide variety of capture devices. Potentially useful alternative capture devices may include, but are not limited to, helix groups, cryogenic tips, barbed hooks, cages, adhesive structures, suction, laser energy, RF energy, etc. Examples of some potentially suitable capture devices and/or systems may be described in U.S. Pat. No. 7,338,434; U.S. Pat. No. 7,141,057; U.S. Pat. No. 7,276,235; U.S. Pat. No. 6,206,827; etc.

The capture device 20 depicted in FIG. 1 includes electrodes that can be used to detect EGM signals for navigating the delivery device 10 and the capture device 20. The particular arrangement of electrodes depicted in connection with the system of FIG. 1 includes electrodes 32, 34, and 36. The electrode 32 may be located on an external surface 21 of the jaw 22 (where the external surface 21 is the surface of the jaw 22 that faces away from the opposing jaw 24). The electrode 34 may be located on an internal surface 23 of the jaw 22 (where the internal surface 23 is the surface of the jaw 22 that faces the opposing jaw 24). The electrode 36 may be located on an internal surface 25 of the jaw 24 (where the internal surface 25 is the surface of the jaw 24 that faces the opposing jaw 22). The electrodes may be placed in any suitable location along the length of the jaws, e.g., the distal end, proximal end or any intermediate location.

The proximal end of the capture device 20 preferably includes connectors connected to each electrode on the distal end of the capture device 20 by leads such that the electrodes can be connected to a system capable of generating user-readable plots of the electrical energy detected using the electrodes. Such systems will be well-known to those of skilled in the art. For example, when inside the pericardial space, the electrodes at the working or distal end of the capture device 20 can be used to detect the electrogram (EGM) on the epicardial surface of the patient's heart. Any or all of the electrodes may be monopolar or multipolar, as desired.

Figure 2A:
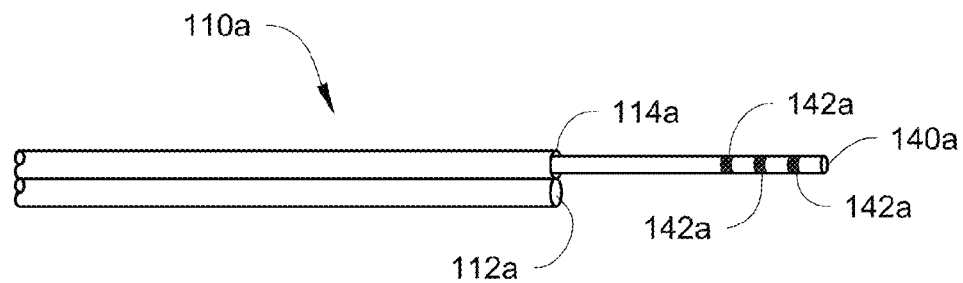
FIG. 2A depicts another exemplary embodiment of a delivery device including a mapping device extending therefrom.

FIG. 2A depicts another system that may be used to navigate to and capture selected tissue. In this depicted embodiment, the delivery device 110a includes two lumens 112a and 114a, with the lumen 112a preferably being used to delivery a capture device (not shown). The lumen 114a is used to deliver a mapping device 140a that, in the depicted embodiment, can be extended out of the lumen 114a.

The mapping device 140a may be in the form of, e.g., a conventional electrophysiology mapping catheter. The mapping device 140a may include as few as one electrode 142a or two or more electrodes 142a. The electrode or electrodes 142a may be monopolar or multipolar.

Although the delivery device 110a could be used with a capture device deployed down the lumen 112a as described above, the delivery device could potentially include a capture device delivered through the same lumen as the mapping device 140a (with the mapping device being deployed, e.g., through a channel provided in the capture device itself). Secondly the device in FIG. 2 may be used independently to find the left atrial appendage based on the electrocardiogram (EGM) and then held in place while a second stabilization/capture device (mechanical grasper, helix group, cryo tip, barbed hook) was deployed to the same location (e.g., over the mapping device 140a or over the delivery device 110a) to grab/stabilize the required tissue.

Figure 2B:
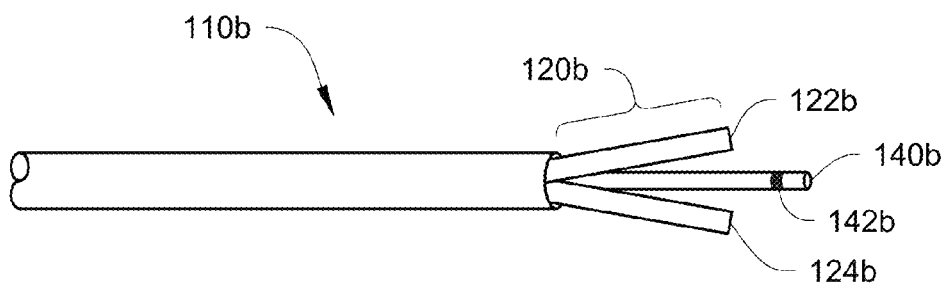
FIG. 2B depicts another exemplary embodiment of a delivery device with a capture device extending out of a delivery lumen in the delivery device and a mapping device extending out of the capture device.

An embodiment in which a mapping device 140b is delivered through a lumen provided in the capture device 120 itself is depicted in FIG. 2B. The mapping device 140b may preferably include an electrode 142b at its distal-most end and/or merely proximate its distal-most end. The capture device 120b may include jaws 122b and 124b that may be used to grasp tissue as described herein. The jaws 122b and 124b and/or the delivery device 110b may or may not include electrodes to assist with navigation.

In the embodiment depicted in FIG. 2B, the capture device 120b may include, for example, a capture shaft (see, e.g., FIGS. 18-20) that includes a lumen through which the mapping device 140b can be advanced and/or retracted. In use, the mapping device 140b may be advanced ahead of the capture device 120b to detect electrical signals in tissue that would then be contacted by the capture device 120b if it were advanced over the mapping device 140b.

Although the depicted embodiment includes a capture device 120b with open jaws, in some embodiments, the capture device may be retained in a closed position while the mapping device is advanced through the closed capture device. In still another variation, the capture device 120b may even be retained within the delivery device 110b while the mapping device 140b is advanced out of the delivery device 110b.

Figure 3:
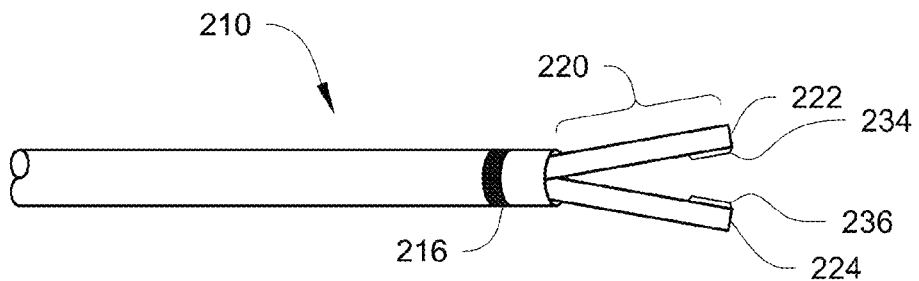
FIG. 3 depicts another exemplary embodiment of a delivery device with a capture device extending out of a delivery lumen in the delivery device.

FIG. 3 depicts another exemplary embodiment of a navigation and tissue capture system that includes a delivery device 210 and a capture device 220. In most respects, the delivery device 210 and the capture device 220 are similar to those depicted and described in connection with FIG. 1. Among the differences are that the delivery device 210 itself includes an electrode 216 located near or proximate its distal end. Although only one electrode 216 is depicted, the delivery device 210 may include two or more electrodes. Also, any electrodes included with the delivery device 210 may be monopolar or multipolar. The electrode 216 may be in the form of a ring electrode as depicted. Alternatively, the electrode or electrodes provided on the delivery device 210 may not be in the form of ring electrodes.

The capture device 220 depicted in FIG. 3 also includes electrodes 234 and 236 on the internal surfaces of the jaws 222 and 224. Although not depicted, the capture device 220 may include other electrodes on, e.g., one or more of the external surfaces of the jaws 222 and 224. The electrode 216 on the delivery device 210 may potentially be used in conjunction with electrodes 234 and 236 on the jaws 222 and 224 to improve navigation and/or to establish the position of the distal end of the capture device 220. The electrode 216 on the delivery device 210 could be used by the operator to help differentiate between tissue (e.g., ventricular and atrial tissue) before the capture device 220 is extended out of the delivery device 210.

One potential advantage of the system depicted in FIG. 3 may be that the distal end of the delivery device 210 could be less traumatic (e.g., softer, smoother, etc.) to the surrounding tissue (e.g., the epicardial surface of the heart) than the capture device 220. After the distal end of the delivery device 210 is in or near a selected internal body location (e.g., the pericardial space) the delivery device 210 (which may preferably be steerable/deflectable) could be navigated to a selected location using the electrode 216 on the delivery device 210 (while the capture device 220 and its electrodes remain in the delivery device 210).

After the distal end of the delivery device is in or near the selected tissue to captured, the capture device 220 may be deployed from the delivery device 210. The electrode or electrodes on the capture device may then be used (alone or in conjunction with the electrode 216 on the delivery device 210) to navigate the capture device 220 to the selected tissue. The electrodes on the capture device 220 may, for example, be able to more accurately assess tissue differentiation. The electrode 216 on the delivery device may, for example, be monitored to determine if the delivery device 210 moves during deployment and use of the capture device 220 (for example, a change in EGM signal seen using the electrode 216 during the grasping of the left atrial appendage may indicate that the delivery device 210 has moved to a less desirable location).

Figure 4:
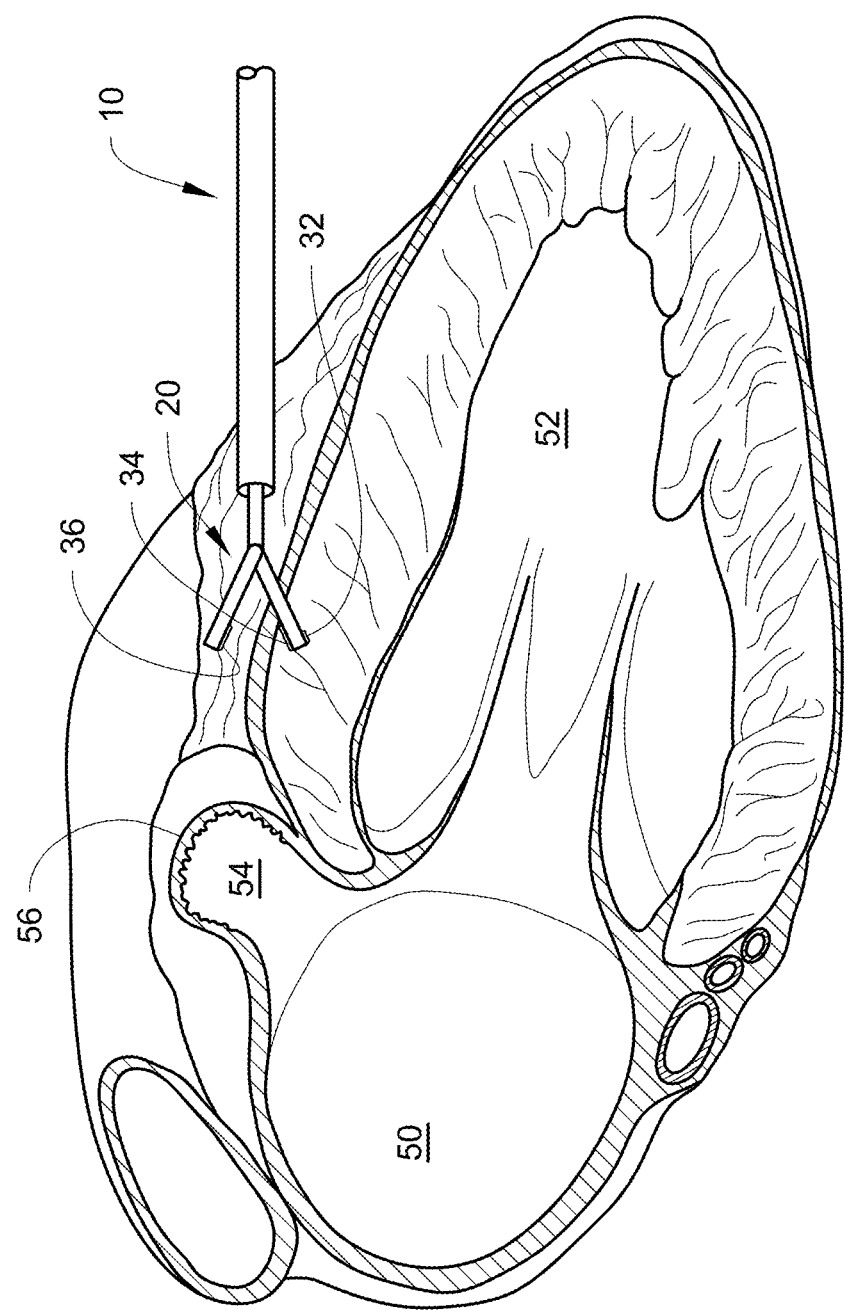
FIG. 4 is a cross-sectional view of a human heart showing the left side anatomy, with the delivery device and capture device of FIG. 1 on the epicardial surface of the human heart.

A cross-sectional view of the left side of the human heart is depicted in FIG. 4 and will be used to describe operation of one embodiment of a navigation and tissue capture system. The heart as depicted includes the left atrium 50 and left ventricle 52. The left atrial appendage 54 extends from the left atrium 50 and includes a distal tip or leading edge 56.

Also depicted in FIG. 4 is the navigation and capture system of, e.g., FIG. 1 including a delivery device 10 and a capture device 20. The capture device 20 includes an external electrode 32 on an external surface of one jaw of the capture device 20 and a pair of internal electrodes 34 and 36 on the internal surfaces of the jaws. The delivery device 10 is depicted as approaching the left atrial appendage 54 from the apex of the heart (which would be typical for a sub-xiphoid approach).

The distal end of the capture device 20 is advanced along the epicardial surface (over, e.g., the left ventricle 52) towards the leading edge 56 of the left atrial appendage 54. As can be seen in FIG. 4, a capture device 20 that progresses along the epicardial surface coming from the apex of the heart is primarily in contact with ventricular myocardium tissue 52 until it reaches the leading edge 56 of the left atrial appendage 54. Although not depicted in FIG. 4, there is a thin pericardial membrane that covers the entire epicardial surface of the heart. This pericardial membrane is electrically inactive and does not produce an independent EGM signal.

Ventricular epicardial myocardium tissue 52 produces a distinct EGM compared with the EGM produced by atrial epicardial myocardium tissue such as that found in the leading edge 56 of the left atrial appendage 54. As the capture device 20 advances across the ventricular epicardial myocardium tissue 52 on the epicardial surface of the heart, the electrodes 32 and 36 will primarily capture only ventricular EGM signals. Although not depicted, the delivery device 10 may, itself, also include one or more electrodes (as, for example, described in the system of FIG. 3). Such electrodes may be used in addition to or in place of the electrodes on the capture device 20 (which may or may not be extended out of the delivery device 10).

Depending on the orientation, number, and/or positions of the various electrodes, it may be possible to detect non-ventricular signals on some of the electrodes. For example, electrode 36 may not be in contact with any ventricular tissue and, thus, may detect a minimal EGM signal, while the electrode 32 may be in direct contact with the ventricular myocardium 52 and would likely show a strong near-field ventricular EGM signal.

The device can optionally be designed to maintain orientation such that any one electrode could be maintained in one stationary location relative to a selected part of the anatomy. With respect to FIG. 4, for example, it may be desirable to keep electrode 32 on the epicardial surface versus on the pericardium. That positioning could potentially be maintained by monitoring the electrode 32 and manipulating the devices such that a strong near-field ventricular EGM signal is continually detected by the electrode 32. In another alternative, if no external electrode 32 is provided on the capture device 20, an operator could, for example, monitor the electrodes 34 and 36 on both jaws of the capture device 20 to determine whether the EGM signal detected from one electrode indicates that its jaw is located closer to the ventricular tissue than the other jaw (or that both jaws show an equal signal strength indicating that both jaws are equally close to the ventricular tissue).

Figure 5:
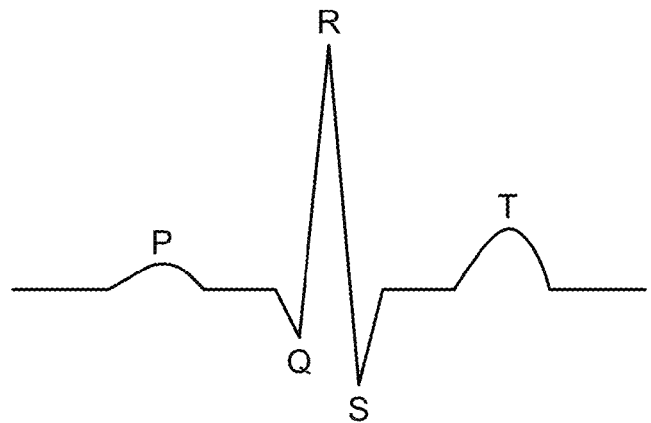
FIG. 5 depicts an exemplary EGM signal from of a normal heartbeat (or cardiac cycle) including a P wave, a QRS complex and a T wave. The EGM signal corresponds to the depolarization of the atria and ventricles.
Figure 6A:
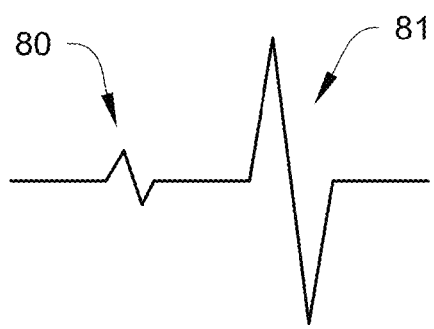
FIGS. 6A-6C depict exemplary electrocardiogram (EGM) signals seen as a device is advanced from the apex of the human heart towards the left atrial appendage.
Figure 6B:
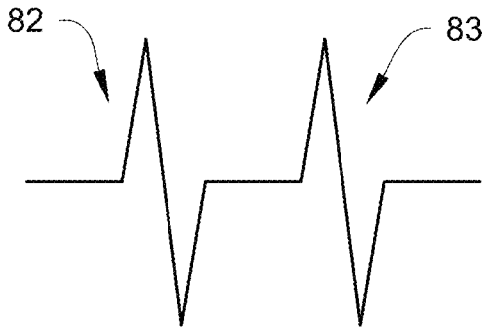
Figure 6C:
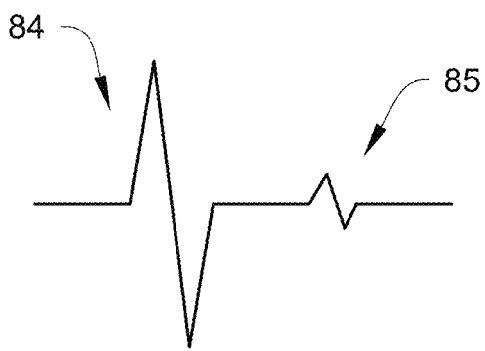

The typical EGM signal associated with a normal human heartbeat (or cardiac cycle) includes a P wave, a QRS complex and a T wave as depicted in FIG. 5. FIGS. 6A-6C depict the EGM signals that may be detected in various locations over the heart. The differences in the EGM signals can be used to determine the position of the electrodes (and thus the devices carrying them) relative to the anatomy of the heart. In some instances, it may be helpful to obtain an electrocardiogram (ECG) signal (using, e.g., surface electrodes as is known conventionally) in addition to the intracardiac EGM signals. The ECG signal may then potentially be used to assist in the navigation process (by, e.g., signal subtraction, etc.).

FIG. 6A represents a potential EGM signal at the initial access point of the sub-xiphoid approach near the apex of the heart. At the apex of the heart there will be a small or insignificant atrial EGM signal (P wave) 80 and a much more pronounced higher amplitude and strong ventricular signal (QRS complex) 81. When the recording electrode is at the apex of the heart or near primarily ventricular tissue the P wave (atrial electrical signal) 80 is much weaker and the QRS complex (ventricular electrical signal) 81 is much stronger with higher amplitude on the EGM tracing.

FIG. 6B depicts a typical EGM tracing as an electrode approaches both atrial and ventricular epicardial tissue. The P wave 82 in FIG. 6B has a much larger amplitude as the electrodes come in contact with atrial tissue (i.e., larger than when the electrodes are at the apex of the heart as seen in FIG. 6A). The QRS complex 83 of FIG. 6B continues to have a large amplitude due to continued contact with ventricular tissue.

FIG. 6C depicts the typical EGM tracing potentially seen using electrodes that are in contact with only atrial tissue such as, e.g., the tissue of the left atrial appendage (which produces strong atrial EGM signals). The EGM signal of FIG. 6C shows a large amplitude P wave 84 and a relatively small amplitude QRS complex signal 85. If the capture device is in the form of a grasping apparatus including jaws, the electrodes that could produce the signal seen in FIG. 6C may be on opposing sides of the left atrial appendage, with the left atrial appendage tissue captured between the jaws. In such an arrangement, capture of electrically active tissue (such as the left atrial appendage) can be distinguished from the capture of electrically inactive tissue (such as, e.g., the pericardium, epicardial fat pads, etc.) using the electrodes on the interior surfaces of the jaws.

Distinguishing between the different EGM signals may preferably be performed by the operator (e.g., the physician), although, in some systems and methods, the distinguishing may be performed with the assistance of an automated system that compares the detected EGM signals with those associated with one or more desired outcomes.

FIG. 7 is another cross-sectional view of a human heart depicting the left-side anatomy in which the navigation/capture system depicted in FIG. 4 is advanced further towards the left atrial appendage 54. Recording electrodes 34 and 36 on the capture device 20 are in direct contact with the epicardial surface of the left atrial appendage 54. The electrode 32 on the external surface of the capture device 20 is still in contact with ventricular tissue.

As a result, the EGM signals detected from the external electrode 32 would differ from the EGM signals detected using the internal electrodes 34 and 36. The different EGM signals would provide a user with the ability to determine that the capture device 20 had, in fact, captured left atrial appendage tissue. Left atrial appendage tissue is the first tissue that produces an atrial EGM when approaching the left atrium from the apex of the heart through a sub-xiphoid access point.

The EGM signal detected between electrodes 34 and 36 would show a strong near-field P wave with high amplitude (atrial electrical activity) and a small amplitude QRS complex (ventricular electrical activity) as depicted in FIG. 8A. In contrast, the external electrode 32 would show a large amplitude QRS complex and potentially and either small or large amplitude P wave depending on its contact with left atrial appendage tissue as depicted in FIG. 8B. It should be noted that the space between the epicardial surface of the heart in the pericardial sac is often full of fluid which may be electrically conductive and may distort the EGM signal slightly when not in direct contact with myocardial tissue.

FIG. 7 provides an opportunity to visualize how the systems and methods described herein may allow the operator to navigate from the apex of the heart (where initial contact is with the epicardial surface during a sub-xiphoid approach) to the tip of the left atrial appendage. As the delivery device 10 (and associated capture device 20) advance across the surface of the heart, the initial EGM signals will indicate contact with ventricular tissue (see, e.g., FIG. 6A). The first EGM signal indicating contact with atrial tissue when approached from the apex of the heart (using, e.g., sub-xiphoid access) should be the tissue of the left atrial appendage.

Further guidance to supplement the use of EGM signals during the procedure may be obtained using other imaging/guidance modalities such as, e.g. fluoroscopy, direct visualization, ultrasound imaging, MRI imaging, CT scans, etc. The use of a secondary imaging/guidance technique may be used to potentially confirm capture of the left atrial appendage by, e.g., providing information regarding the angle of closure of the jaws of a grasping apparatus, etc. If, for example, no tissue is captured, then the jaws of a grasping apparatus may close completely. When tissue is present, the jaws will typically not close completely.

Figure 9:
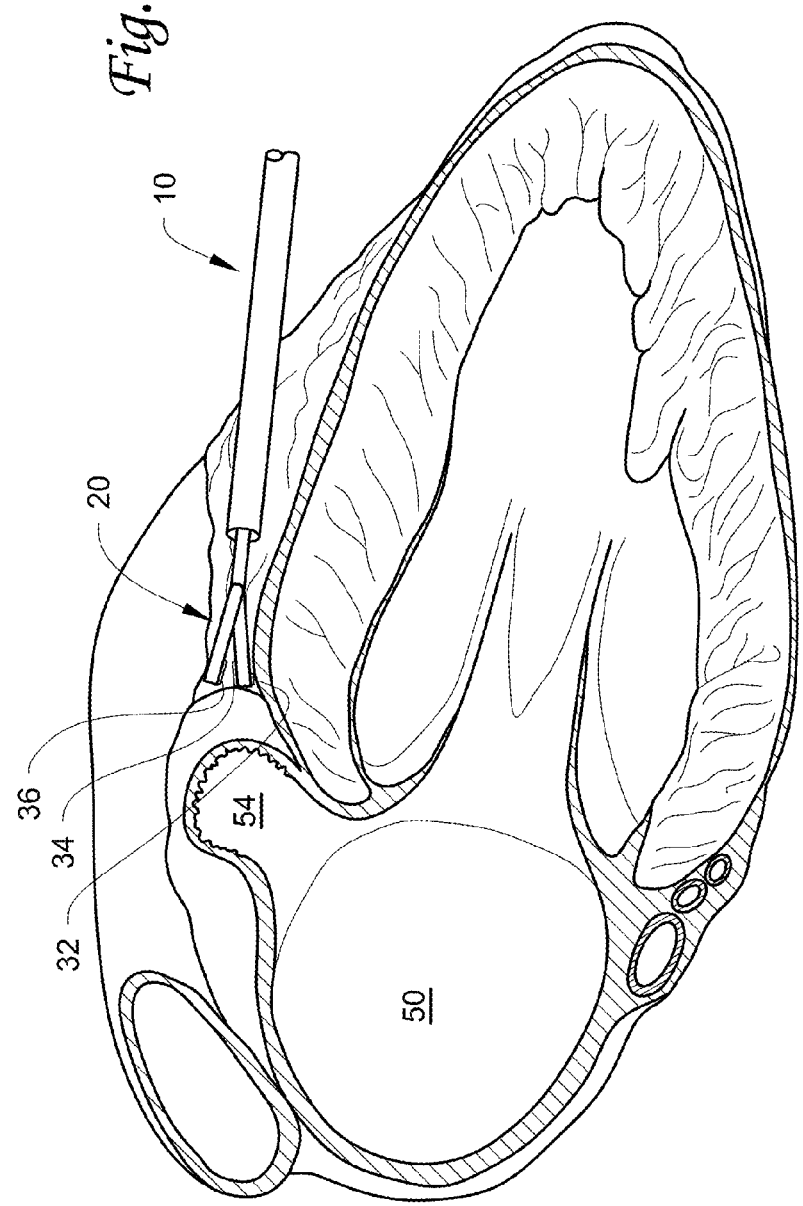
FIG. 9 is a cross-sectional view of the human heart depicting closure of the capture device of FIG. 1 in a situation where the capture device does not capture left atrial appendage tissue.
Figure 10A:
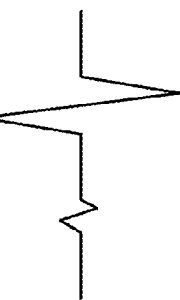
FIG. 10A depicts a representative electrogram (EGM) across the interior electrodes on the jaws of the capture device of FIG. 9 when the jaws do not capture tissue.

FIG. 9 depicts a situation in which the capture device 20 (and associated delivery device 10) of FIG. 4 is advanced towards the left atrial appendage, but is closed without capturing the tissue of the left atrial appendage. One potential benefit of using EGM signals to navigate to and/or confirm capture of the left atrial appendage tissue is that when the electrodes on a capture device 20 close without capturing tissue between them, the EGM signal would not show a strong amplitude P wave. Rather, the electrodes 34 and 36 would be expected to short out and show a flat line EGM signal as depicted in FIG. 10A because the electrical potential across the electrodes 34 and 36 is zero. If the operator only grabs a small portion of the left atrial appendage tissue in the capture device 20, there also may not be enough impedance, with the result being, again, a flat line EGM signal as depicted in FIG. 10A. In this case, an operator could re-open the capture device 20 and reposition it until the electrodes 34 and 36 indicate a strong amplitude P wave and corresponding contact with left atrial appendage tissue.

Figure 10B:
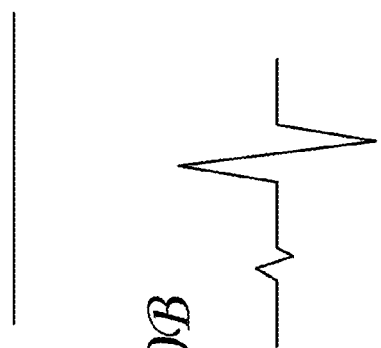
FIG. 10B depicts a representative electrogram (EGM) as detected using the exterior electrode when the jaws do capture left atrial appendage tissue.

In the situation depicted in FIG. 9, the external electrode 32 on the capture device 20 would typically be expected to show a large amplitude QRS complex and potentially and either small or large amplitude P wave depending on its contact with left atrial appendage tissue as depicted in FIG. 10B.

Figure 11:
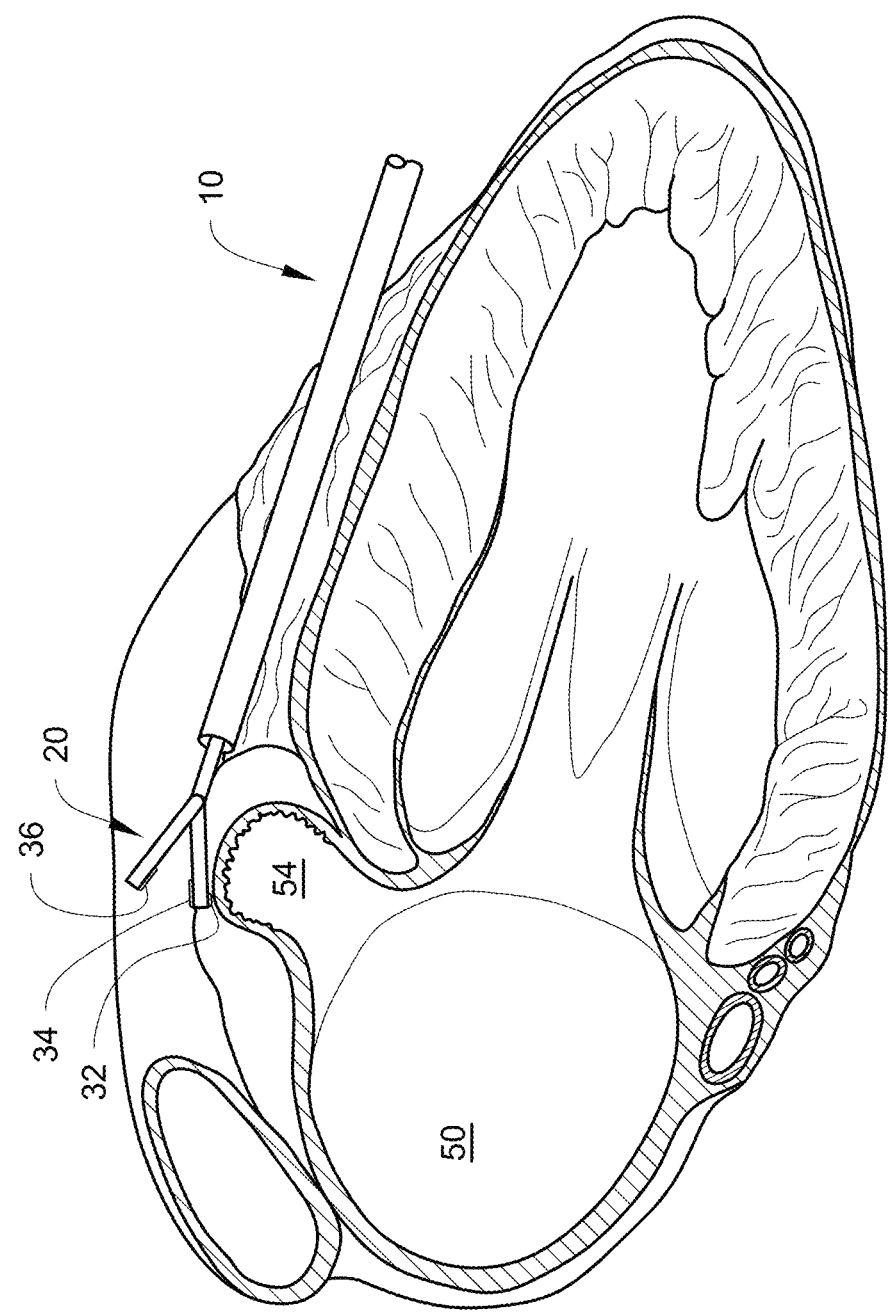
FIG. 11 is a cross-sectional view of the human heart depicting advancement of a capture device past the distal tip of the left atrial appendage lobe.

FIG. 11 depicts another situation in which the capture device 20 (and associated delivery device 10) are advanced too far. When the capture device 20 is advanced past the tip of the left atrial appendage that is closest the apex of the heart, it will likely not come into contact with any other atrial tissue. Any tissue that is captured by the capture device 20 as depicted in FIG. 11 will have an non-atrial EGM signal. The electrodes 34 and 36 on the capture device 20 may, for example, reflect an EGM signal of the pericardium or far-field ventricular and/or atrial signals. The external electrode 32 on the capture device 20 may reflect a strong atrial EGM signal given that it may still be in contact with the left atrial appendage as the capture device 20 passes over the appendage (which may be an indication that the capture device 20 is incorrectly positioned). When the LAA is properly positioned in the capture device 20, the external electrode 32 should detect at least some ventricular EGM signal as discussed herein.

Figure 12:
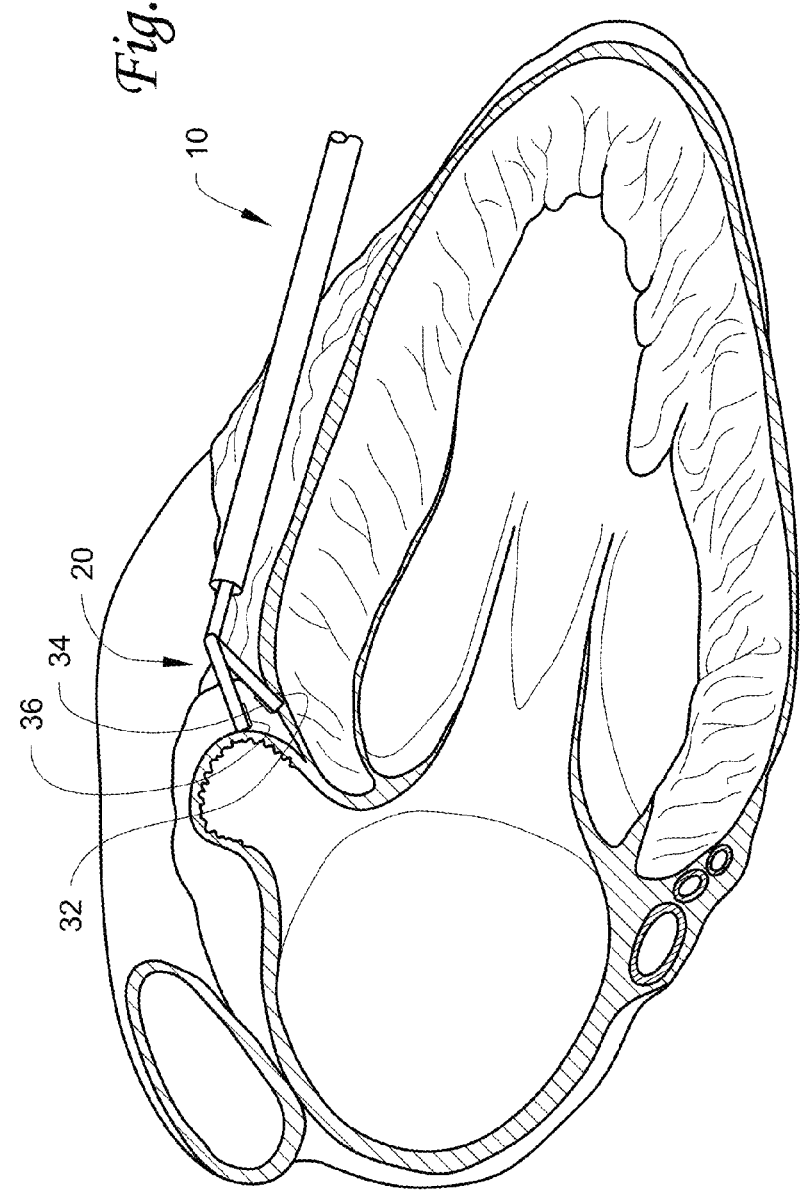
FIG. 12 is a cross-sectional view of the human heart depicting the capture device after advancement beneath the distal tip of the left atrial appendage lobe.

FIG. 12 depicts another situation in which the capture device 20 (and associated delivery device 10) are advanced into a position that is not amenable to proper capture of the left atrial appendage. In this situation, the capture device 20 is depicted as advanced beneath the tip of the left atrial appendage, such that the capture device 20 is located between the left atrial appendage and the underlying ventricular tissue. In such an arrangement, it would be unlikely that the capture device 20 could properly capture left atrial appendage tissue for a subsequent procedure. Tissue that is captured when the capture device 20 is beyond the position depicted in FIG. 12 could likely be ventricular tissue with a ventricular EGM signal across electrodes 34 and 36 on the capture device 20.

Figure 13A:
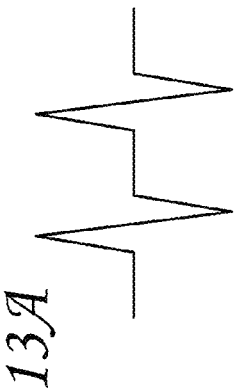
FIG. 13A depicts a representative electrogram (EGM) across the interior electrodes on the jaws of the capture device of FIG. 12.
Figure 13B:
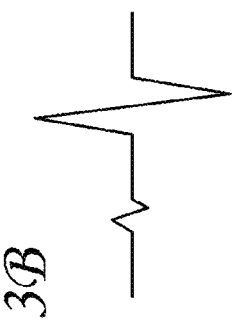
FIG. 13B depicts a representative electrogram (EGM) as detected by the exterior electrode on the capture device of FIG. 12.

Confirmation of the situation depicted in FIG. 12 could potentially be obtained if the EGM signals from the electrodes 34 and 36 on the capture device showed both atrial and ventricular signatures as depicted in, e.g., FIG. 13A. In addition, the external electrode 32 may, if it located nearest the ventricular tissue, show an EGM signal weighted towards the QRS complex portion of the complete EGM signal as depicted in FIG. 13B.

The situation depicted in FIG. 12 may not, however, be entirely hopeless. The capture device 20 could potentially capture a lobe of the left atrial appendage and this could be a clinically acceptable outcome. Confirmation of this outcome could potentially be obtained by, e.g., detecting a strong atrial EGM signal (see, e.g., FIG. 6C) using the electrodes 34 and 36 on the capture device 20.

Figure 14:
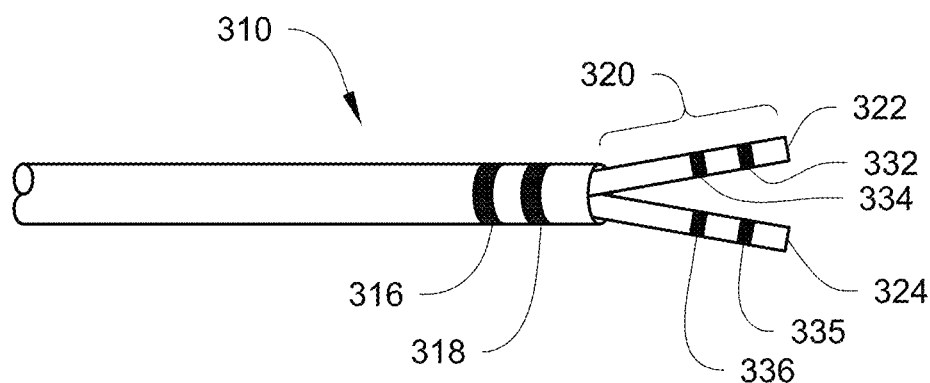
FIG. 14 depicts another exemplary embodiment of a delivery device with a capture device extending out of a delivery lumen in the delivery device.

FIG. 14 depicts another exemplary embodiment of a delivery device 310 and a capture device 320 similar to those depicted in FIGS. 1 and 3. Unlike the devices in those figures, the electrodes 316 and 318 on the delivery device 310 and the electrodes 332, 333, 334, and 335 on the capture device 320 are all ring electrodes. The ring electrodes 316 and 318 on the delivery device 310 could, however, be used in conjunction with electrodes on the jaws 322 and 324 to improve navigation to the left atrial appendage by potentially more precisely establishing position of the distal ends of the jaws 322 and 324 of the capture device 320. Any or all of the electrodes could be monopolar or multipolar.

The electrodes 316 and 318 on the delivery device 310 could be used by the operator to help differentiate between the ventricular and atrial tissue as the delivery device 310 is advanced. Additional specificity of EGM interpretation is potentially feasible with the electrode configuration depicted in FIG. 14. For example, reading a bi-polar signal across electrode 332 and 334 on jaw 322 or electrode 335 and 336 on jaw 324 may allow the operator to better confirm the presence of particular types of tissue within the capture device 320 (i.e., ventricular tissue versus atrial tissue).

The electrodes on the jaws 322 and 324 of the device depicted in FIG. 14 may also create a near-field EGM. The near-field EGM signal may produce a cleaner and easier to interpret EGM signal for determination of tissue type. The ring electrodes 316 and 318 on the delivery device 310 could be used for navigation in the pericardial space in a similar manner as described above for the device depicted in FIG. 3, yet with the potential for a more precise near-field EGM created from the two ring electrodes 316 and 318.

Figure 15:
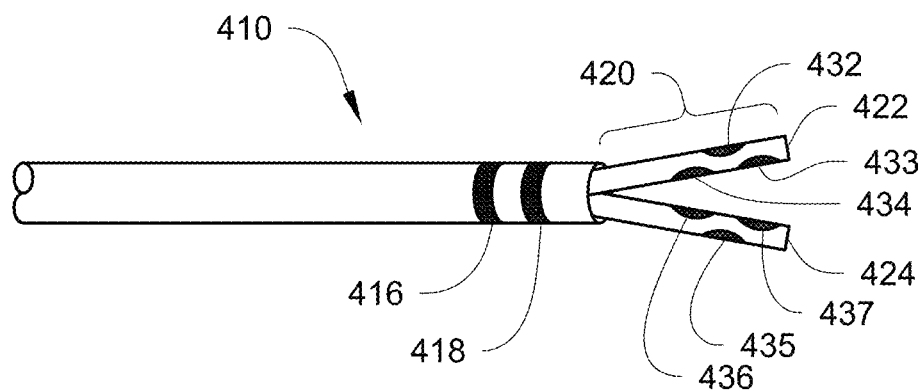
FIG. 15 depicts another exemplary embodiment of a delivery device with a capture device extending out of a delivery lumen in the delivery device.

Another potential embodiment depicted in FIG. 15 includes ring electrodes 416 and 418 on the delivery device 410. The electrodes 433, 434, 436, and 437 on the internal surfaces of the jaws 422 and 424 could be used to help better navigate and position the capture device 420. The external electrodes 432 and 435 on the external surfaces of the jaws 422 and 424 could be used to differentiate tissue on the external surface of the jaws 422 and 424 from that in contact with the internal surfaces of the jaws. Electrodes 433 and 434 on jaw 422 and electrodes 436 and 437 on jaw 424 only capture the near-field EGM signal on the internal grasping surfaces of the jaws. External electrodes 432 and 435 may be used to determine the position of the capture device 420 relative to the pericardium, ventricular tissue underneath the LAA or any other tissue. Any or all of the electrodes could be monopolar or multipolar.

With the ability to differentiate tissue on the external surface versus the internal surface of the capture device 420, the configuration of electrodes on the capture device 420 may provide additional specificity of EGM interpretation versus the configuration seen in the device of FIG. 14. The ring electrodes 416 and 418 on the delivery device 410 could again be used for navigation in the pericardial space in a similar manner as described for similar arrangements herein (with the potential for a more precise near-field EGM read from the two ring electrodes 416 and 418).

Figure 16:
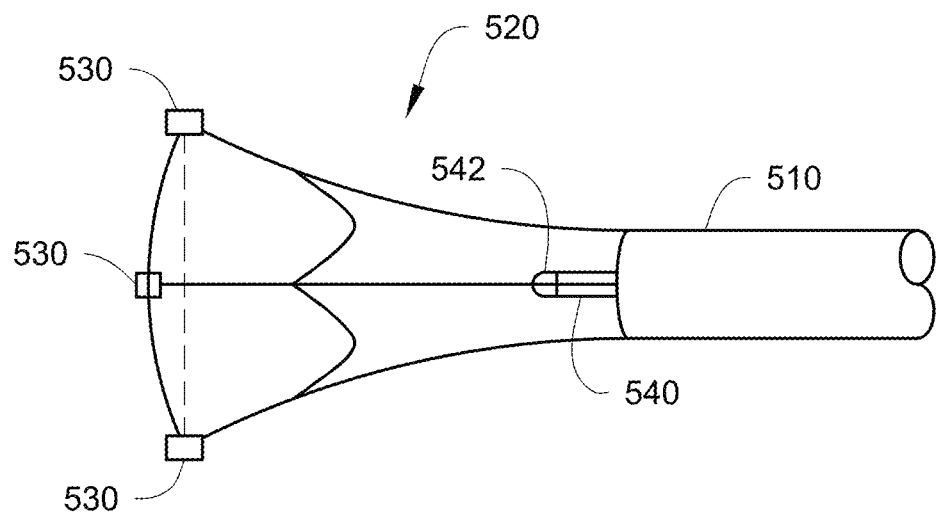
FIG. 16 depicts another exemplary embodiment of a delivery device with a capture device and a guiding element extending out of a delivery lumen in the delivery device.

In addition to the examples described herein, navigation and tissue capture systems described herein may be integrated into known tissue capture systems. Examples of some potentially suitable tissue capture systems including delivery devices and capture devices may be described in U.S. Patent Application Publication No. US 2007/0073313 (Liddicoat et al.). One example (depicted in FIG. 16) of a capture device 520 according to the principles described in Liddicoat et al. may, for example, include electrodes 530 integrated with the supports or guides included in the disclosed devices. The capture device 520 may preferably be delivered using a delivery device 510. The system of FIG. 16 may also include an optional guide element 540 which may include an electrode 542 in place of or in addition to a magnet as described in Liddicoat et al. If the guiding element 540 is provided with an electrode 542, the electrodes 530 on the capture device 520 may be optional.

Figure 17:
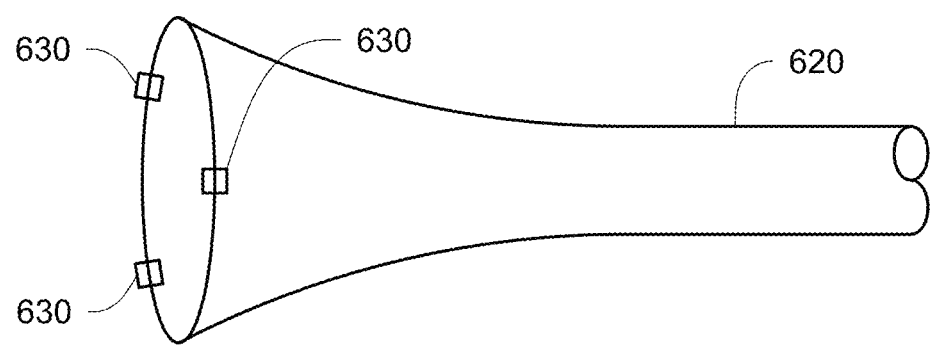
FIG. 17 depicts another exemplary embodiment of a capture device.

Yet another exemplary embodiment of a capture device 620 is depicted in FIG. 17 in the form of a catheter that includes a lumen that may be used to provide suction to capture tissue. The capture device 620 may include one or more electrodes 630 proximate (at or near) the distal end of the catheter to detect physiological electrical activity to guide the capture device as described herein. The capture device 620 may also (or alternatively) include one or more electrodes that are spaced from the distal end of the capture device 620 as described herein with respect to, e.g., the embodiments depicted in FIGS. 18-20.

Figure 18:
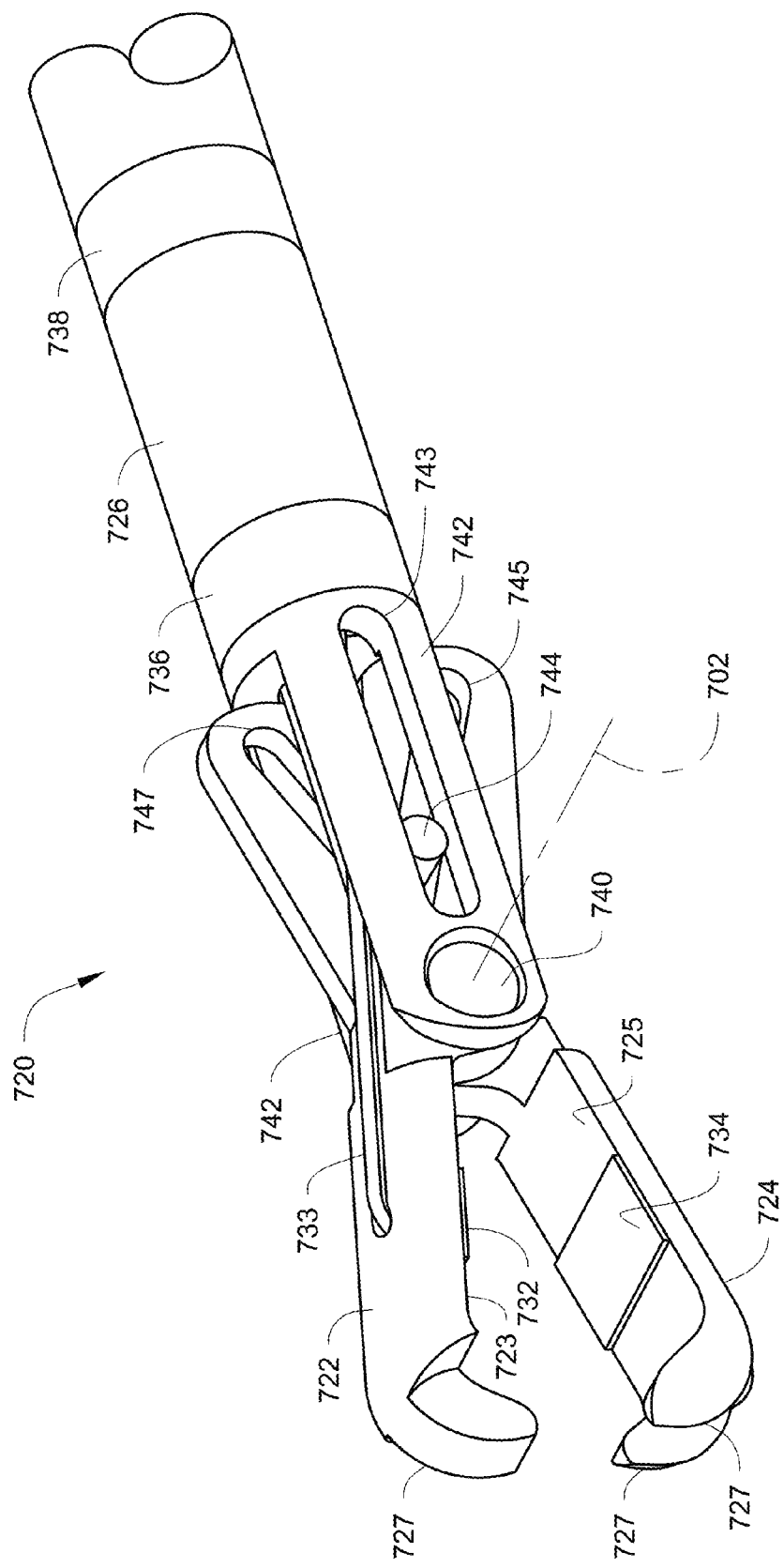
FIG. 18 is an enlarged perspective view of the distal end portion of one embodiment of a capture device in an open configuration.

Still another exemplary embodiment of a capture device 720 that may be used in the systems and methods described herein is depicted in connection with FIG. 18. The capture device 720 includes a first jaw 722 and a second jaw 724. The first and second jaws 722 and 724 may be mounted on the distal end of a capture shaft 726 that can be used to advance the capture device 720 through the lumen of an introducer, endoscope, catheter, trocar, etc. that can provide access to a selected internal body location.

The capture devices of systems and methods described herein may preferably operate in an atraumatic manner to capture tissue. As used herein, "atraumatic" (and variations thereof) means that the capture devices described herein, when used to capture tissue, do not cut, sever, or remove the captured tissue. In other words, the capture devices used in connection with the systems and methods described herein can be distinguished from conventional biopsy devices because the capture devices described herein preferably do not cut, sever, and/or remove of tissue as would conventional biopsy devices. The capture devices may, however, include retention structures/features such as serrations, teeth, roughened surfaces, posts, pins, adhesives, etc. that contribute to the ability of the capture devices to maintain attachment to tissue captured within the jaws while still remaining an atraumatic device.

In the depicted embodiment of the capture device 720, one example of a retention structure is found in the complementary teeth 727 found on the jaws 722 and 724. The depicted retention structure includes one tooth 727 located on the first jaw 722 and two teeth 727 located on the second jaw 724. The tooth 727 on jaw 722 may preferably nest within the pair of teeth 727 to assist in retaining tissue within the capture device 720.

The first jaw 722 of capture device 720 has an interior surface 723 that faces the interior surface 725 of the opposing second jaw 724. Also included in the depicted embodiment of capture device 720 is a first electrode 734 positioned on the interior surface 723 of the first jaw 722 and a second electrode 736 positioned on the interior surface 725 of the second jaw 724.

As described herein, the capture device 720 may have a closed configuration in which the jaws are closed such that the interior surfaces 723 and 725 of the first and second jaws 722 and 724 move towards each other and an open configuration (see, e.g., FIG. 18) in which the first and second jaws are open and spaced apart such that the capture device can capture tissue between the jaws 722 and 724.

The capture device may optionally include a mechanism to lock the jaws in the closed configuration such that a user is not required to continually hold the capture device 720 in the closed configuration. The locking mechanism may preferably be operable from the proximal end of the capture device. In one embodiment, the locking mechanism may take the form of a biased (e.g., spring-loaded, etc.) mechanism that holds the jaws of the capture device in a closed configuration in the absence of any intervening force that is applied to open the jaws. Such an embodiment may be referred to as having "normally-closed" jaws.

In still other embodiments, the jaws of a capture device may alternatively be biased (e.g., spring-loaded, etc.) in an open configuration in the absence of an intervening force that is applied to close the jaws. Such an embodiment may be referred to as having "normally-open" jaws. Such jaws may be closed to capture tissue using any suitable mechanism including, but not limited to a sheath that can be advanced distally over the jaws, thereby urging them into a closed configuration.

Referring to, e.g., FIG. 1 in addition to FIG. 18, the capture device 720 may also have a delivery configuration in which the distal end of the capture device 720 (typically the jaws 722 and 724) is contained within the capture lumen of a delivery device such as a sheath, introducer, endoscope, catheter, trocar, etc. The capture device may further have an extended configuration in which the distal end of the capture device 720 extends out of the capture lumen of a delivery device proximate the distal end of the delivery device. This concept is also described above in connection with FIG. 1.

In the depicted embodiment, the jaws 722 and 724 are both attached for rotation about an axis 702 that is oriented generally transverse to a longitudinal axis 701 that extends from a proximal end to a distal end of the capture shaft 726. The axis of rotation 702 about which the jaws 722 and 724 rotate may not necessarily be exactly transverse to the longitudinal axis 701 in any or all planes that contain the longitudinal axis 701.

Figure 19:
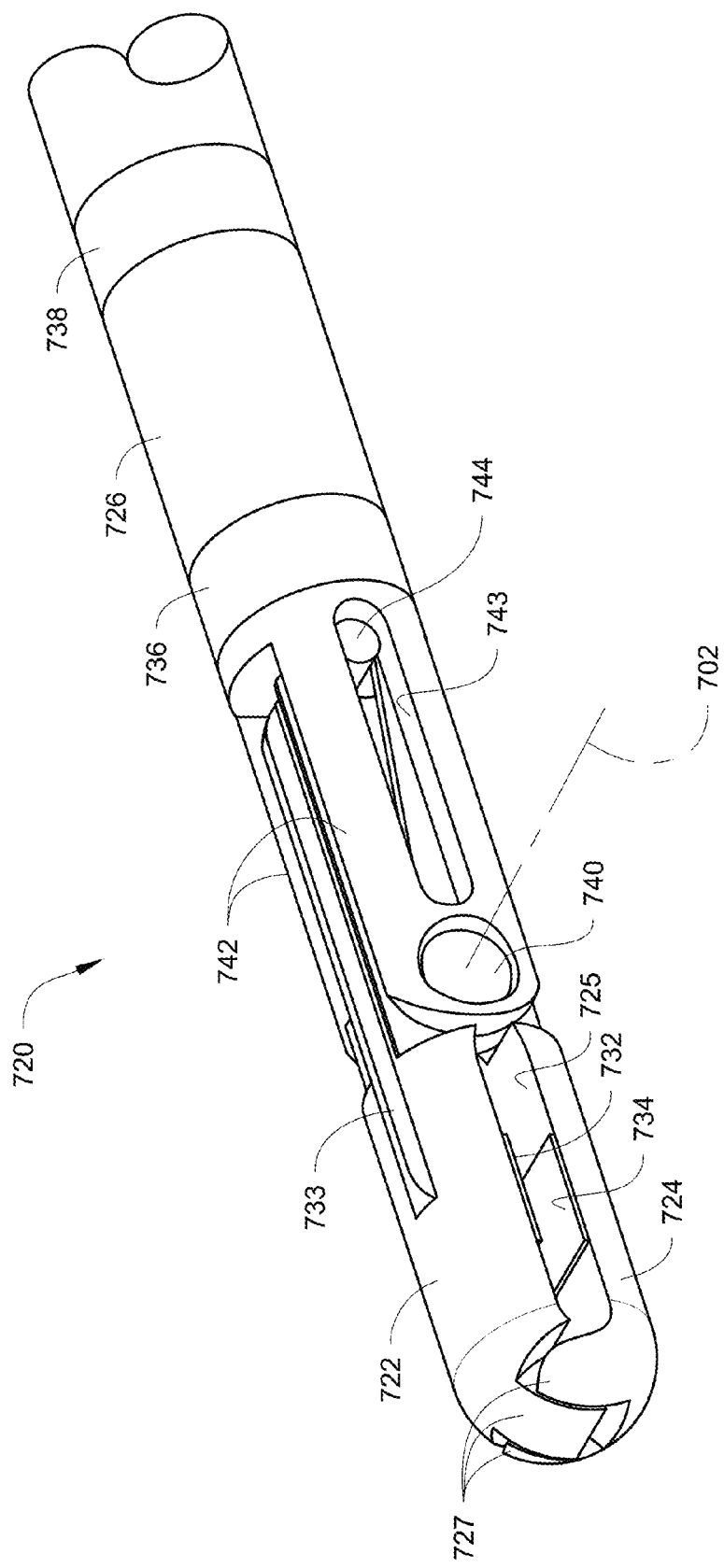
FIG. 19 is an enlarged perspective view of the capture device of FIG. 18 in a closed configuration.
Figure 20:
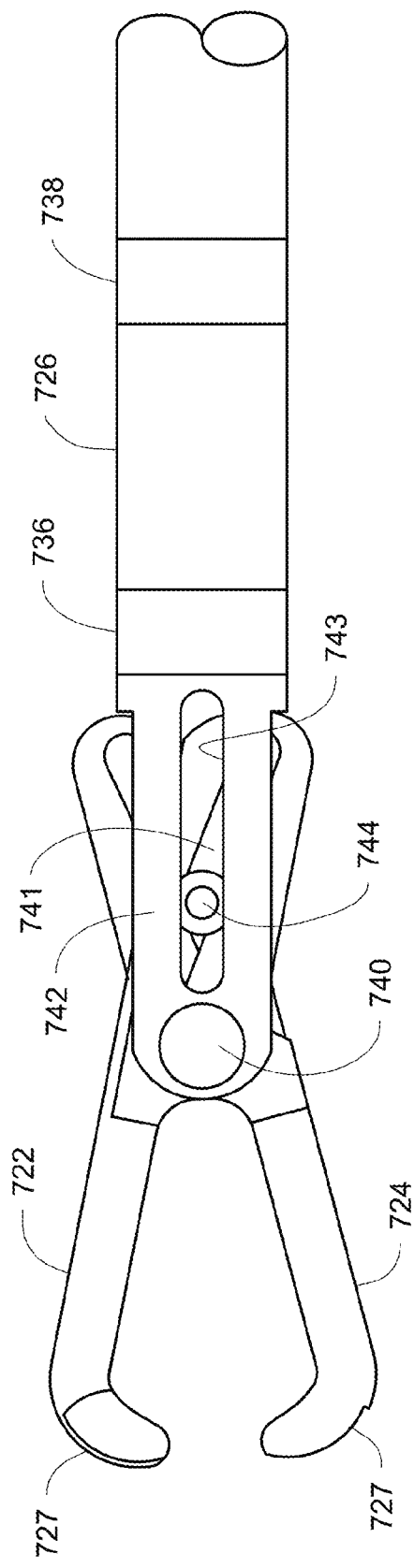
FIG. 20 is a side elevational view of the capture device of FIG. 18.

Movement of the jaws 722 and 724 between the open and closed configurations can be accomplished by a wide variety of different mechanisms. FIGS. 18-20 depict only one example of a potentially suitable mechanism. In the depicted embodiment, rotation of the jaws 722 and 724 about the axis 702 means that the jaws 722 and 724 are pivotally mounted on a main rivet 740 that extends through arms 742 that extend from the capture shaft 726. Axis 702 (about which the jaws 722 and 724 rotate) preferably extends through the main rivet 740.

Rotation of the jaws 722 and 724 about the axis 702 is effected in the depicted embodiment by moving a link rivet 744 through slots 743 formed in arms 742. Movement of the link rivet 744 is effected, in the depicted embodiment, by moving an actuator such as a drive rod 741 through an actuator lumen in the capture shaft 726, with the link rivet 744 being attached to the drive rod 741. The link rivet 744 also extends through slots 745 and 747 located in the jaws 722 and 744. As the link rivet 744 is advanced distally towards the distal end of the capture device 720 (see, e.g., FIGS. 18 and 19), the jaws 722 and 724 open. Conversely, as the drive rod 741 and attached link rivet 744 are moved proximally, the jaws 722 and 724 close (see, e.g., FIG. 20).

The capture device 720 also includes a variety of electrodes that can be used to monitor EGM signals. The depicted embodiment of the capture device 720 includes a first electrode 732 located on the interior surface 723 of the first jaw 722 and a second electrode 734 located on the interior surface 725 of the second jaw 724.

A first electrode lead 733 extends from the first electrode 732 towards a proximal end of the capture device 720. The first electrode lead 733 is connected to the electrode 732, in the depicted embodiment, through the jaw 722 with a similar lead being located on the second jaw 724 (but not depicted in FIGS. 18 and 19). The leads may preferably extend through the capture shaft 726 where they terminate at an EGM monitoring apparatus connector (not seen).

A potential alternative structure for electrically connecting the electrodes 732 and 734 without using separate and discrete leads as seen in FIGS. 18 and 19 may include placing the main rivet 740 in electrical communication between a coil (other conductor) extending through the capture shaft 726, the first jaw 722, and electrode 732. The main rivet 740 is preferably electrically isolated from the second jaw 724 and its electrode 734 by any suitable technique, e.g., insulating washers, bushings, etc. (which may be constructed of dielectric materials such as, e.g., polyimides, PEEK, etc.). Similarly, the link rivet 744 may serve as the path for electrical communication between another lead (such as the drive rod 741), the second jaw 724, and electrode 734. The link rivet 744 may also be electrically isolated from the first jaw 722 and its electrode 732 by any suitable technique, e.g., insulating washers, bushings, etc. (which may be constructed of dielectric materials such as, e.g., polyimides, PEEK, etc.).

Although the jaws 722 and 724 may be made of electrically conductive materials (such as, e.g., metals, etc.), they may be coated with nonconductive materials such that, e.g., the electrodes 732 and 734 on selected surfaces, e.g., the outer surfaces, etc. Some potentially suitable nonconductive materials may include polymers, paints, epoxies, etc. Insulating the outer surfaces and other areas of the capture devices may potentially enhance the ability of the system to capture and/or distinguish EGM signals of tissue located within the capture device. In some embodiments, the electrodes provided on the capture devices may be in the form of discrete electrodes that are attached to the capture device (e.g., a jaw, etc.) as depicted in, e.g., FIGS. 18-19. Where the capture device elements on which the electrodes are placed are electrically conductive, the electrodes may be electrically isolated from the capture device.

The electrodes 732 and 734 may, in some embodiments, be located on the interior surfaces 723 and 725 of the jaws 722 and 724 such that the electrodes are located opposite from each other. In such a configuration, closure of the jaws 722 and 724 in the absence of tissue or other material located therein may preferably result in electrical communication between the electrodes, e.g., the electrodes 732 and 734 may "short out" when the jaws 722 and 724 are closed. Such an event may be useful for providing an indication to a user that not tissue has been captured by the capture device 720.

Another optional feature that may be described in connection with the embodiment of the capture device 720 depicted in FIGS. 18 and 19 is that the electrodes used on the jaws of the capture device 720 may occupy substantial portions of the interior surfaces of the jaws. For example, it may be preferred that the electrodes 732 and/or 734 occupy about one quarter or more of the interior surfaces 723 and 725 of the jaws. In some embodiments, it may be further preferred that at least one of the electrodes provided on the interior surface of a jaw occupy about one half or more of the interior surface of the jaw.

Although the capture device 720 includes a pair of electrodes, with one electrode located on each jaw, it should be understood that that many different electrode configurations are possible. For example, only one electrode may be provided such that, e.g., only one of the jaws carries an electrode (with a return electrode located elsewhere, e.g., on the capture shaft, an exterior surface of one of the jaws, on a delivery device, etc.). In some embodiments, for example, an electrode is coupled to the interior surface of a first jaw and the interior surface of a second jaw is free of any electrodes.

In another example, two or more electrodes may be placed on one jaw, while the other jaw contains no electrodes. The two or more electrodes may be provided in any suitable configuration, e.g., they may be arranged along a straight line, in a circle, randomly, etc. An example of an embodiment in which only one of the jaws carries electrodes may be seen with reference to FIG. 15 where the capture device 420 may be provided with only one set of interior electrodes (e.g., only electrodes 433 and 434, but not electrodes 436 and 437). In such an embodiment, the opposing interior surface of the opposing jaw may be electrically conductive such that closure of the jaws places the two electrodes in electrical communication with each other (i.e., shorts out the electrodes) to provide an indication that no tissue is captured between the jaws. The electrically conductive interior surface may be inherent in the opposing jaw (if, e.g., the interior surface was exposed metal or some other conductive material) or the opposing interior surface may be provided with a conductive element on its interior surface that is placed to provide the desired shorting out function.

Still another optional feature depicted in connection with, e.g., the capture device 720 depicted in FIGS. 18-20 is the use of electrodes on the capture shaft 726. As seen in FIGS. 18 and 19, the capture shaft 726 includes a pair of shaft electrodes 736 and 738. The shaft electrodes 736 and 738 may be used to, e.g., monitor the type of tissue in contact with the shaft 726. As discussed herein, the EGM signals picked up by electrodes used with the capture devices described herein can be useful in determining the location of the device within, e.g., the pericardial space. For example, the shaft electrode(s) 726 may potentially be used in the same manner as the external electrodes on capture devices described in connection with FIGS. 4-13.

The shaft electrodes 736 and 738 may or may not be provided in the form of ring electrodes that extend around the perimeter of the shaft 726. The electrodes 736 and 738 may preferably be electrically isolated from the remainder of the capture device 720 and be placed in electrical communication with EGM monitoring apparatus through leads that extend proximally through the capture shaft 726.

Although two shaft electrodes 736 and 738 are depicted in connection with the capture device 720, the capture devices may be provided with only one shaft electrode, three or more shaft electrodes, and even no shaft electrodes. If provided, the one or more shaft electrodes may preferably be located within a distance of about 10 centimeters (cm) or less, about 5 cm or less, or even about 2 cm or less from the distal end of the capture device such that the EGM signals detected using the shaft electrodes are those that are indicative of the tissue proximate the working portion of the capture device.

The function of the shaft electrodes may, in some instances be provided and/or supplemented by using one or more electrodes at other locations, e.g., electrodes located on a delivery device used to deliver the capture device, electrodes on exterior surfaces of the jaws or any other element of any other capture device, electrodes on the skin or at other locations on the subject, etc.

Although the capture devices depicted in FIGS. 18-20 and elsewhere herein include two jaws, both of which may be moved to change between an open and closed configuration, it should be understood that the captured devices may include more than two jaws, e.g., three, four or more jaws. In still other variations, one or more of the jaws may be stationery while one or more of the remaining jaws moves to changed between the open and closed configurations. For example, with respect to the embodiment of FIGS. 18-20, the jaw 722 may be stationary with respect to the capture shaft 726, while jaw 724 rotates to move the capture device between the open and closed configurations.

As described herein, other navigation techniques may be used in combination with EGM-based navigation. An exemplary embodiment of an additional method of navigating a device to an anatomical structure (e.g., the left atrial appendage) may include delivering a device into an anatomical space (e.g., the pericardial sac); injecting image enhancement liquid (e.g., a liquid contrast agent in the case of fluoroscopy, echogenic liquids for use in conjunction with ultrasonic imaging, etc.) into the anatomical space (e.g., the pericardial sac); and identifying the location of the device and/or the locations of anatomical structures (e.g., the left atrial appendage) using any appropriate imaging modality, e.g., fluoroscopic visualization, MRI, CT scanning, etc. In some embodiments, this method and apparatus used to perform it could be used alone, i.e., without the aid of EGM-based navigation.

Although this method of navigating a device to an anatomical structure may be utilized for many anatomical structures (e.g., any structure relating to the epicardial surface of the heart such as various veins and arteries, fat pads, structural defects, etc.), the following description, for simplicity, describes the use of the method and device for navigating to and/or outlining the left atrial appendage (LAA).

Figure 21:
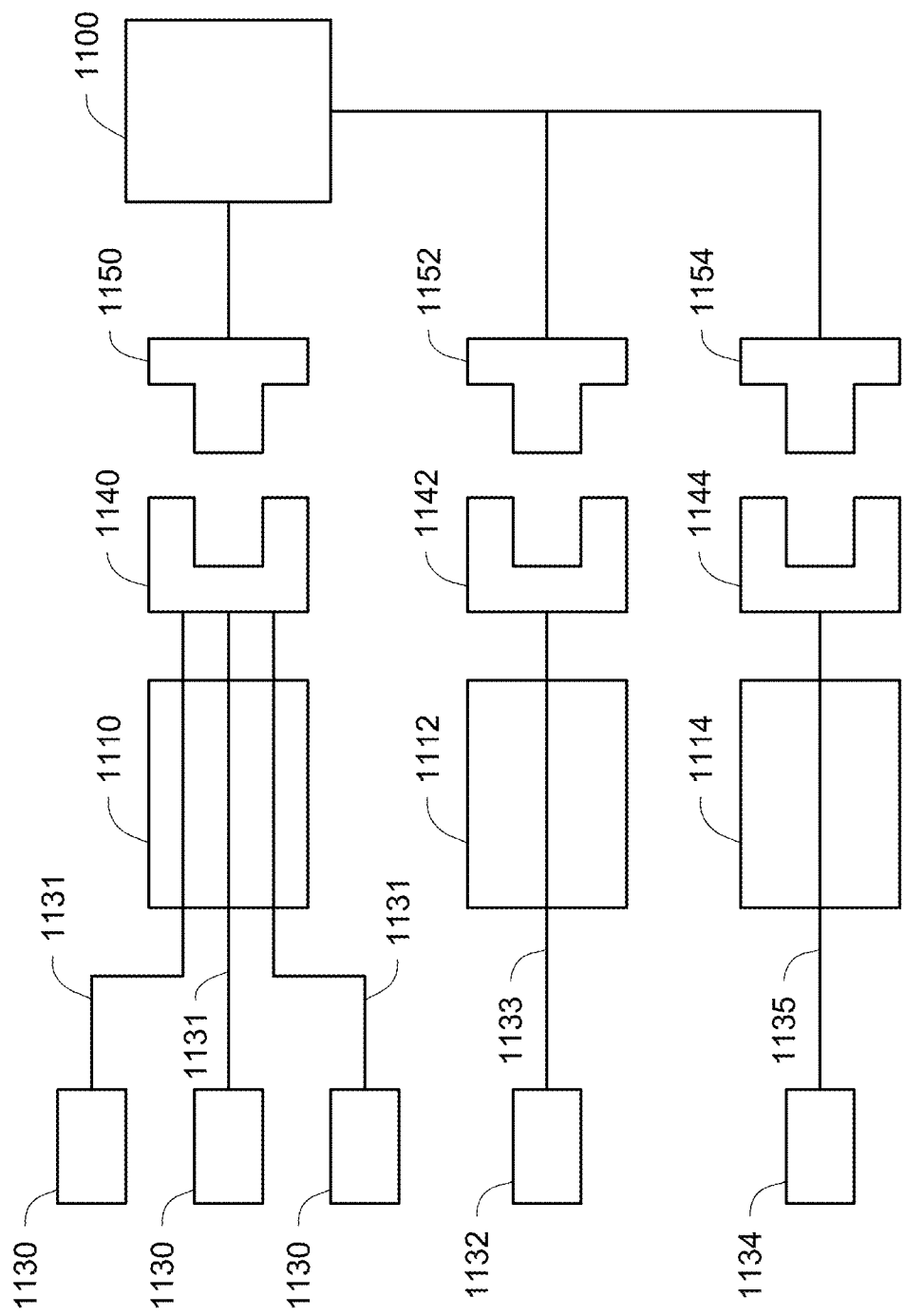
FIG. 21 is a schematic of one system including electrodes operably connected to an electrical activity (e.g., EGM) monitoring device.

A system level schematic is depicted in FIG. 21 to show potential connections between electrodes and other components that may be used with tissue navigation and capture systems described herein. The depicted system includes a capture device 1110 having one or more electrodes 1130 and connector 1140 connected to the electrodes 1130 through leads 1131. The depicted system optionally also includes a delivery device 1112 that may include an electrode 1132 (or more than one electrode) and a connector 1142 connected to the electrode 1132 through a lead 1133 and a reference device 1114 that may include a reference electrode 1134 (or more than one electrode) and a connector 1144 connected to the electrode 1134 through a lead 1135. For example, the reference device 1114 may be endocardial or epicardial lead for obtaining cardiac electrical signals. Further, for example, the reference device 1114 may be a body-surface electrode (e.g., for attachment to the skin of a subject) for obtaining cardiac electrical signals.

The connectors 1140, 1142, and 1144 may be adapted to connect to an electrical (e.g., EGM, etc.) monitoring device 1100 through connectors 1150, 1152, and 1154. As a result, innate electrical signals that may be detected by the electrodes may be monitored, displayed, analyzed, filtered, stored, manipulated, enhanced, etc. to assist a user in navigating the delivery device and/or capture device as described herein. The connectors may take any suitable form, e.g., plugs, sockets, bare wires, snap-fit connectors, etc.

FIGS. 22-25 depict configurations and methods of the navigation and tissue capture systems described herein (e.g., the system described with reference to FIGS. 1-21). The navigation and tissue capture system may include, in some embodiments, a capture device, a capture shaft (e.g., including an elongated body extending from a proximal end to a distal end, wherein the distal end of the capture shaft is attached to the capture device), and one or more primary electrodes attached to the capture device and/or the ligation element used in connection with the capture device. The system may further include a secondary electrode and electrical monitoring apparatus operably connected to the primary electrode(s) and the secondary electrode(s).

The secondary electrode, in some embodiments, may be a body-surface electrode locatable on a body surface. A body-surface electrode may monitor ECG signals that, e.g., may be useful to differentiate atrial EGM signals from un-wanted signals, e.g., ventricular EGM signals.

In some embodiments, the secondary electrode may be an electrode attached to a delivery device. The delivery device may include a proximal end, a distal end, and a delivery lumen. The delivery lumen may include an opening proximate the distal end of the delivery device and the capture device and the capture shaft may be sized for movement within the delivery lumen of the delivery device. Further, the capture device may include a delivery configuration in which a distal end of the capture device is contained within the delivery lumen and an extended configuration in which the distal end of the capture device extends out of the delivery lumen proximate the distal end of the delivery device. The delivery device may allow recording/monitoring/detecting of a ventricular signal with the secondary electrode. For example, when accessing the LAA from a sub-xiphoid approach, the secondary electrode of a delivery device will generally be located proximate ventricular tissue and not atrial tissue. As a result, the secondary electrode attached to a delivery device may reliably monitor EGM signals from ventricular tissue, which may be used to enhance the primary signal and/or to assist in determining what EGM signals the primary electrode is receiving (e.g., to determine where the capture device is located).

Still further, the system may include an endocardial/epicardial device and the secondary electrode may be attached to such device. The endocardial/epicardial device may be separate from the capture device and may be located so as to place the secondary electrode proximate a selected cardiac tissue (e.g., high right atrium, right ventricular apex, left pulmonary artery, right ventricular outflow tract (RVOT EGM signals may be able record far-field LAA EGM signals), etc.) to, e.g., record EGM signals to enhance the primary signal and/or to assist in determining what EGM signals the primary electrode is receiving (e.g., to determine where the capture device is located). When utilizing the endocardial/epicardial device, an operator may confirm that the secondary electrode is located proximate the selected tissue and restrain the device in place such that any movement of the capture device will not upset the placement of the secondary electrode, thereby maintaining contact between the selected tissue and the secondary electrode for consistent secondary signal monitoring.

In some embodiments, the methods of the previous paragraph may be more generally described as: placing a secondary electrode in proximity to known tissue to obtain a secondary signal; place the primary electrode in proximity to unknown tissue to obtain a primary signal; use the primary signal and secondary signal to make a determination as to the type of the unknown tissue proximate the primary electrode. In other embodiments, the secondary electrode may be placed more remotely from cardiac tissue (e.g., on the body surface, etc.) such that the secondary signal includes the entire cardiac cycle, including P wave, QRS complex and T wave.

Figure 22:
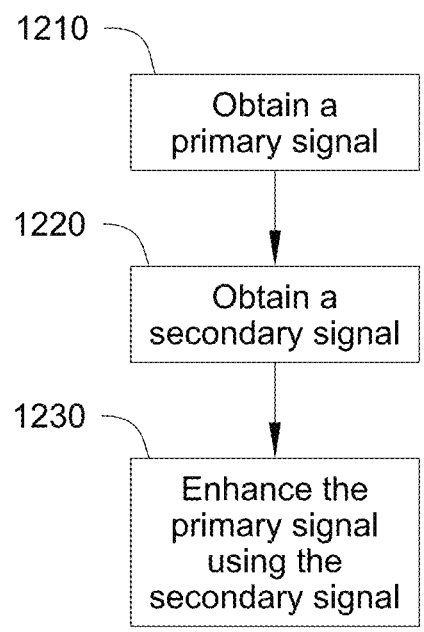
FIGS. 22-25 are block diagrams of methods and configurations to be used with the navigation and tissue capture systems described herein.

As shown in FIG. 22, the electrical monitoring apparatus may be configured to: obtain a primary signal by monitoring cardiac electrical activity using the primary electrode (block 1210); obtain a secondary signal by monitoring cardiac electrical activity using the secondary electrode (block 1220); and enhance the primary signal using the secondary signal to assist in determining the location of the capture device (block 1230). The electrical monitoring apparatus may enhance the primary signal in many different ways, some examples of which are described below with reference to FIGS. 23-25.

For example, the electrical monitoring apparatus may be configured to filter signals (e.g., parasitic signals, noise, contaminant ventricular electrograms, etc.) from the primary signal. In at least one embodiment, the electrical monitoring apparatus may filter (e.g., blank, subtract-out, reduce, minimize, shade, etc.) signal(s) from the primary signal obtained when the secondary signal indicates ventricular activity (e.g., a QRS complex—see, e.g., FIG. 5) to enhance the primary signal. The primary signal may, for example, be monitoring EGM signals from atrial tissue which may have relatively small QRS complexes and relatively large P waves, and as a result, the QRS complexes and P waves may be difficult to differentiate. Therefore, the secondary signal may be used to determine when the QRS complexes occur such that the QRS complexes within the primary signal may be removed leaving only EGM activity due to atrial EGM activity.

In some embodiments, the electrical monitoring apparatus may be configured to determine a ventricular time period based on the secondary signal (e.g., the ventricular time period may start at the onset of the QRS complex and end at the subsidence of the QRS complex, the ventricular time period may start at the onset of a QRS complex and end at the onset of a P wave, the ventricular time period may include pre-specified number of milliseconds before and after any ventricular signal detection, etc.) and limit monitoring of the primary signal to time periods that fall outside of the ventricular time period to enhance the primary signal. Further, the electrical monitoring apparatus may be configured to remove or otherwise attenuate at least a portion of the QRS complex of the primary signal to enhance the primary signal by using the secondary signal.

In addition to or in place of filtering that takes the form of signal subtraction, the systems and methods described herein may be configured to otherwise attenuate the primary signal to enhance the usefulness of the primary signal as an indicator that selected tissue (e.g., the left atrial appendage) has been captured or is proximate the capture device. Such attenuation may take the form of, e.g., shading the portion of the signal corresponding to the QRS complex and/or the P wave (to, e.g., enhance a user's ability to discern between the two portions of the signal), displaying the different portions of the primary signal in different colors, enhancing and/or reducing the amplitude of portions of the primary signal based on timing relative to the QRS complex and/or the P wave (e.g., amplifying the P wave portion or reducing the amplitude of the portion corresponding to the QRS complex timing), etc.

Figure 23:
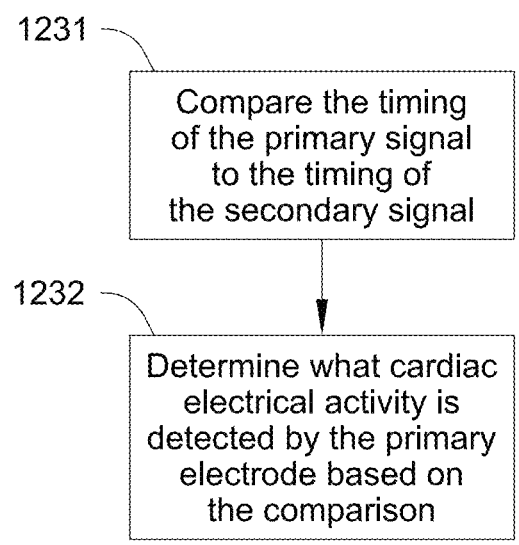

The electrical monitoring apparatus may, in some embodiments, be configured to determine what cardiac electrical activity is detected by the primary electrode (e.g., the primary signal) based on the timing (e.g., frequency, etc.) of the primary signal relative to a known secondary signal as depicted in FIG. 23. Such configuration may be useful to determine the location of the capture device relative to various cardiac structures (e.g., the LAA). For example, the electrical monitoring apparatus may be configured to compare the timing of the primary signal to the timing of the secondary signal (block 1231) and determine what cardiac electrical activity is detected based on the comparison between timing of the primary signal and the timing of the secondary signal (block 1232). After the electrical monitoring apparatus determines what cardiac electrically activity is detected by the primary electrode, the electrical monitoring apparatus may be configured to indicate the detected cardiac activity to an operator. For example, the electrical monitoring apparatus may indicate to an operator that the primary electrode is receiving atrial EGM signals, which, e.g., indicates that the capture device may be located proximate and/or may have captured atrial tissue.

Where, for example, the secondary signal is obtained from known tissue (e.g., ventricular tissue, atrial tissue, etc.) and the timing between the primary signal and the secondary signal is the same, a conclusion may be drawn that the two signals are obtained from similar tissue (e.g., atrial, ventricular, etc.). Where, for example, the secondary signal is obtained from known tissue (e.g., ventricular tissue, atrial tissue, etc.) and the timing between the primary signal and the secondary signal are different, a conclusion may be drawn that the two signals are obtained from different tissue (e.g., atrial versus ventricular, etc.). In still another embodiment where the secondary signal is placed such that it includes the entire cardiac cycle, the timing comparison may be made between the primary signal and one or more selected portions of the secondary signal to make a determination as to the type of tissue providing the primary signal through the primary electrode.

In at least one embodiment, the electrical monitoring apparatus may be configured to compare the timing of the P wave component of the primary signal to the timing of the P wave component of the secondary signal and determine what cardiac electrical activity is detected by the primary electrode based on the comparison of the timing of the P wave component of the primary signal and the P wave component of the secondary signal. In such an embodiment, if the P wave components of the primary electrode and the secondary electrode are consistent with a determination that the primary signal is detecting atrial EGM signals, then a determination may be made that the primary electrode (and capture device is attached to) is located proximate atrial tissue (e.g., the LAA).

In at least another embodiment, the electrical monitoring apparatus is further configured to compare the timing of the QRS complex component of the primary signal to the timing of the QRS complex component of the secondary signal and determine what cardiac electrical activity is detected by the primary electrode based on the comparison between the timing of the QRS complex component of the primary signal and the timing of the QRS complex component of the secondary signal. In such an embodiment, if the QRS complex components of signals detected by the primary electrode and the secondary electrode are consistent with a determination that the primary signal is detecting ventricular EGM signals, then the primary electrode (and capture device is attached to) may be located proximate ventricular tissue (e.g., the left ventricle).

Further, in some embodiments, the electrical monitoring apparatus may be configured to compare the slew rate of the primary signal to a reference slew rate and/or the slew rate of a secondary signal and determine what cardiac electrical activity is detected by the primary electrode. Such embodiments may be based on the different slew rates that may be found in EGM signals obtained from different types of tissue. Where, for example, ventricular tissue has an EGM with a known slew rate that is different from a known slew rate associated with an EGM signal obtained from atrial tissue, then a comparison of the slew rate of the primary signal may be compared to the known slew rate of the ventricular and/or atrial tissue may be used to determine the type of tissue proximate the primary electrode. For example, if the slew rate of the primary signal is similar to the known slew rate of ventricular tissue, then a determination may be made that the primary electrode is located proximate ventricular tissue. If the slew rate of the primary signal is different from to the known slew rate of ventricular tissue, then a determination may be made that the primary electrode is not located proximate ventricular tissue. In another example, if the slew rate of the primary signal is similar to the known slew rate of atrial tissue, then a determination may be made that the primary electrode is located proximate atrial tissue. If the slew rate of the primary signal is different from to the known slew rate of atrial tissue, then a determination may be made that the primary electrode is not located proximate atrial tissue.

In still other embodiments, the electrical monitoring apparatus may be configured to use slew rate to make a determination regarding the tissue located proximate a primary electrode, various signal enhancement techniques could be used to accentuate any differences in the slew rates being analyzed. Those signal enhancement techniques may include, but are not limited to, addition, subtraction, etc.

In those embodiments in which timing of the different signals and/or portions of signals is used to make a determination as to the tissue proximate the different electrodes, it may be useful to adjust the timing of the signals obtained depending on the location of the primary and secondary electrodes. For example, the timing may be adjusted based on the propagation of EGM signals through the heart (e.g., EGM signals may propagate from the top of the heart or the atrium to the bottom of the heart or the ventricle). As such, a selectable delay may be added to the signals based on where the primary and/or secondary electrodes are located (e.g., body-surface, left ventricle, etc.) to adjust for propagation delays.

Figure 24:
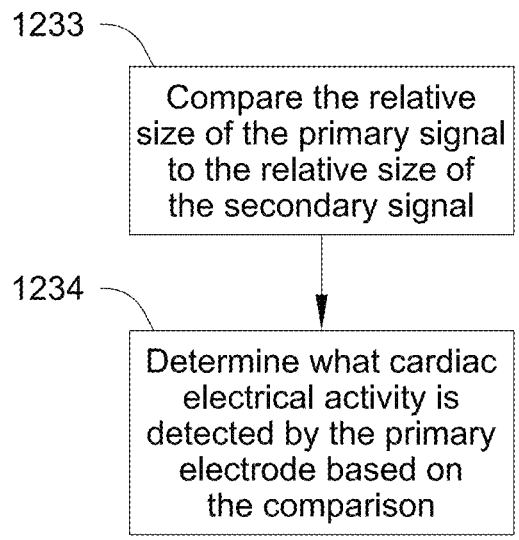

The electrical monitoring apparatus may be configured to determine what type of cardiac electrical activity is obtained by the primary electrode based on the relative amplitudes of the primary signal and the secondary signal as depicted in FIG. 24. For example, the electrical monitoring apparatus may be configured to compare the relative size of the primary signal to the relative size of the secondary signal (block 1233) and determine what type of cardiac electrical activity is detected by the primary electrode based on the comparison between the amplitude of the primary signal and the amplitude if the secondary signal (block 1234). In some embodiments, the electrical monitoring apparatus may alternatively be configured to compare the area under the curve of the primary signal to the area under the curve of the secondary signal to determine what type of cardiac electrical activity is detected by the primary electrode.

Amplitude and/or area of the primary and/or secondary signal curves may be useful in making a determination as to whether the primary electrode is located proximate ventricular or atrial tissue because there is significantly more ventricular tissue than atrial tissue. As a result, the amplitude of the QRS signal from the ventricular tissue is typically greater than the amplitude of a signal obtained directly from atrial tissue. The absolute amplitude of any signal obtained from ventricular tissue should, in almost all cases, be higher than the signal obtained from atrial tissue. In some embodiments, a system configured to make a simple comparison of signal amplitudes irrespective of timing may be sufficient to distinguish between signals obtained from ventricular tissue and atrial tissue.

Figure 25:
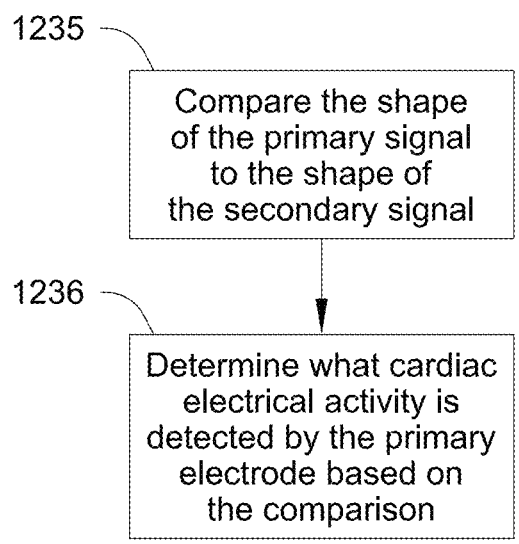

In some embodiments, the electrical monitoring apparatus may be configured to determine what type of cardiac electrical activity is obtained by the primary electrode based on the relative shapes of the primary signal and/or the secondary signal as depicted in FIG. 25. For example, the electrical monitoring apparatus may be configured to compare the relative shape of the primary signal to the relative shape of the secondary signal (block 1235) and determine what cardiac electrical activity is detected by the primary electrode based on the comparison between the relative shape of the primary signal and the relative shape of the secondary signal (block 1236). In at least one embodiment, the electrical monitoring apparatus may be configured to compare the slope of a selected portion of the primary signal to the slope of a selected portion of the secondary signal and determine what cardiac electrical activity is detected by the primary electrode based on the comparison between the slope of the selected portion of the primary signal and the slope of the selected portion of the secondary signal.

Converting the primary and/or secondary signal from the time domain to the frequency domain may also be useful to enhance the primary signal and/or determine what cardiac electrical activity is detected by the primary electrode. For example, the electrical monitoring apparatus may be further configured to generate frequency domain data representative of the primary signal (e.g., utilizing a Fourier transforms, etc.), generate frequency domain data representative of the secondary signal, compare the frequency domain data representative of the primary signal to the frequency domain data representative of the second signal, and determine what cardiac electrical activity is detected by the primary electrode based on the comparison between the frequency domain data representative of the primary signal and the frequency domain data representative. Further, during atrial fibrillation, the frequency of the atrial signals may be markedly different than the frequency of the ventricular signals, and as such, the frequency domain analysis may clearly differentiate atrial signals from ventricular signals (e.g., to assist in locating the capture device relative to atrial or ventricular tissue).

In those embodiments in which various characteristics of the primary signal are described as being compared to characteristics of the secondary signal in an effort to make a determination as to the type of tissue that is located proximate the primary electrode, the use of the secondary signal may be optional. In other words, in some embodiments, the primary signal alone may be used and compared to one or more known reference signals that may be, e.g., stored in the memory of a system as described herein. Some of the characteristics for which a "library" of reference signals may be used for comparison to an obtained primary signal include, for example, slew rate, slope, amplitude, area under a curve, shape of a curve, frequency domain data, etc.

In still other embodiments, one or more of the same characteristics of the primary curve may be analyzed using an algorithm to make a determination as to the type of tissue from which the primary signal is obtained using the primary electrode.

Although described individually herein, any two or more of the various signal enhancement techniques described herein, e.g., filtering, signal subtraction, comparison to a secondary signal or known data (of, e.g., slew rate, slope, amplitude, shape of a curve, area under a curve, frequency domain data, etc.) may be used in combination to assist in distinguishing between atrial and ventricular signal as discussed in connection with the systems and methods described herein. The use of two or more of these techniques may result in a more accurate and/or robust determination as to tissue proximate the primary electrode.

Figure 26:
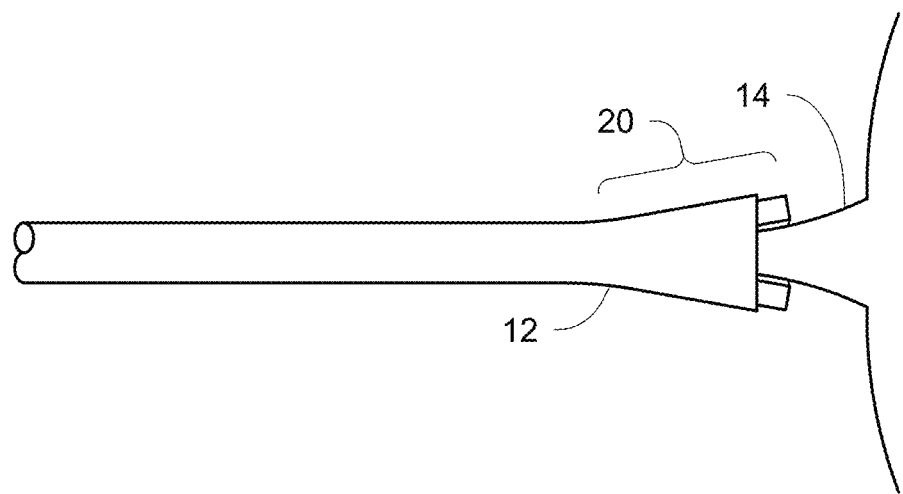
FIG. 26. depicts one exemplary embodiment of a capture device covered by a sheath device.

An additional feature that may assist enhance the primary signal is a sheath device 12 as depicted in FIG. 26. The sheath device 12 may include a proximal end, a distal end, and a sheath lumen. Further, the sheath device 12 may be flexible and formed from any biocompatible material that is capable of at least partially absorb electromagnetic signals. The lumen may include an opening (e.g., along a longitudinal axis extends between the proximal end and the distal end) configured to receive a capture device 20 such that the capture shaft and capture device may be sized for movement within the sheath lumen of the sheath device 12. The sheath device 12 may be used within the systems described herein in a covered configuration where at a least a portion of the capture device 20 is contained within the sheath lumen so as to potentially at least partially electromagnetically shield the one or more electrodes of the capture device. For example, after the capture device 20 has captured tissue 14, the sheath device 12 may be extended to cover at least part of the capture device 20 such that the electrodes located on the capture device 20 are located within the sheath device 12 (The electrodes may be at least partially electromagnetically shielded from EGM signals outside of the sheath device 12 when located in the sheath device 12 so as to enhance the signal obtained from the electrodes located on the capture device 20).

Such configurations and methods for utilizing the navigation and tissue capture systems described herein (e.g., the system described with reference to FIG. 21) may be used with alternative electrode configurations other than a primary electrode attached to the capture device and a secondary electrode attached to a delivery device, to body surface, and to an endocardial/epicardial device. For example, an exemplary navigation and tissue capture system may include a capture device, a capture shaft (e.g., including an elongated body comprising a proximal end and a distal end, wherein the distal end of the capture shaft is attached to the capture device), a shaft electrode attached to the capture shaft proximate the distal end of the capture shaft (e.g., the shaft electrode is located proximally of the capture device such that the shaft electrode is located between the capture device and the proximal end of the capture shaft), a first capture device electrode attached to the capture device and a second capture device electrode attached to the capture device. Further, the electrical monitoring apparatus may be operably connected to the first capture device electrode, the second capture device electrode, and the shaft electrode.

In at least one embodiment, the electrical monitoring apparatus may be configured to obtain a far-field signal by selectively coupling the first capture device electrode and the second capture device electrode as a single conjoint electrode and monitoring electrical activity using the single conjoint electrode and the shaft electrode and obtain a near-field signal by selectively decoupling the first capture device electrode and the second capture device electrode and monitoring electrical activity using the decoupled first capture device electrode and the second capture device electrode. The near-field signal and the far-field signal may be compared (e.g., size, shape, timing, etc.) as described herein, and if the signals are a selectable percentage (e.g., 10%, 20%, 30%, 40%, 50%, 60%, 70%, 80%, 90%, 100%) consistent with a determination that the signal is detecting a selected EGM signal, then the capture device may be located proximate such selected tissue (e.g., if the signals are too similar, then the capture device is probably located proximate ventricular tissue and not atrial tissue/if the signals are not very similar, then the capture device is probably located proximate atrial tissue and not ventricular tissue). Further, the near-field signal and the far-field signal may be used with the same methods and configurations as the primary signal and secondary signal (e.g., the near-field signal may be the primary signal and the far-field signal may be the secondary signal) described above with reference to FIGS. 22-25.

Further, the methods and configurations described herein with reference to FIGS. 22-25 may be used with systems including a single electrode. For example, an navigation and tissue capture system may include a capture device, a capture shaft (e.g., including an elongated body comprising a proximal end and a distal end, wherein the distal end of the capture shaft is attached to the capture device), a primary electrode attached to the capture device, and electrical monitoring apparatus operably connected to the primary electrode.

The electrical monitoring apparatus may be configured to monitor a baseline signal (e.g., an atrial signal) by monitoring electrical activity of selected tissue (e.g., atrial tissue) using the primary electrode and store the baseline signal. Further, the electrical monitoring apparatus may be configured to obtain a primary signal by monitoring electrical activity using the primary electrode, compare the primary signal to the stored baseline signal, and determine what cardiac electrical activity is detected by the primary electrode based on the comparison between the primary signal to the baseline signal. The primary signal and the baseline signal may be used with the same methods and configurations as the primary signal and secondary signal (e.g., the baseline signal may be the secondary signal) described herein with reference to FIGS. 22-15. Further, baseline signals may be any monitored from any tissue producing EGM signals (e.g., ventricular tissue producing EGM signals, atrial tissue producing atrial EGM signals).

Still further, the methods and configurations described herein with reference to FIGS. 22-25 may be used with systems including capture device including a first jaw and a second jaw with each jaw including multiple electrodes. Any of the multiple electrodes on either of the jaws may be coupled in a singular or multi-polar configuration and used using any of the signal processing configurations and methods described herein. For example, bipoles located proximate the center of a jaw may be compared to a corresponding bipole located proximate the center an opposite jaw. Further, bipoles from the center a jaw to bipoles in the center of an opposite jaw may be compared to bipoles located near the edges of the jaws (e.g., the signal monitored in the center may better reflect the tissue located within the jaws).

Among variations that may or may not be explicitly described herein, the following features, components, etc. may be included in the navigation and tissue capture systems described herein. For example, although the devices are depicted as having substantially straight bodies, they may be precurved such that in the absence of an intervening force, the bodies take on a curved shape.

The systems and methods described herein could be used to detect tissues other than the left atrial appendage using other detectable physiological electrical activity that can provide guidance for navigation.

The systems and methods described herein may be used in a manual operation, i.e., where one or more operators manually position the devices described herein. Alternatively, some or all of the devices in the systems and methods described herein may be controlled by automated equipment (e.g., robotically, etc.).

The systems and methods described herein could be used in conjunction with the following surgical techniques: percutaneous, minimally invasive, laparascopic, keyhole, Natural Orifice Transluminal Endoscopic Surgery (NOTES), open surgery, endoscopic surgery, etc. and combinations of two or more of these techniques.

Although described in connection with the human anatomy, the systems and methods described herein could be used with any animal (i.e., have use in both human and veterinary applications).

Although not explicitly depicted, the EGM detection can be performed between any two electrodes or between a single electrode and ground (electrically neutral). Ground can be created by, e.g., placing a patch electrode on a subject's body (or placing another electrode on or on the body) and using it as a reference electrode.

Other Considerations with Respect to Navigation Sensed Electrograms:

When a solitary ventricular electrogram is sensed, the capture and/or delivery device is manipulated in a cephalad direction towards the typically located left atrial appendage or left atrium. If, on further advancement, both ventricular and atrial electrograms are noted, then the tip of the device is either between the overlying left atrial appendage and the underlying left ventricular myocardium (between appendage and LV), or on the mitral annulus. To further distinguish these two possibilities the following may be noted.

First: An equally near field atrial and ventricular electrogram despite movement in a cephalad—caudad direction suggests location between the overlying appendage and the left ventricular myocardium. Whereas, when such movements results in either a larger—more near field atrial electrogram or a larger—more near field ventricular electrogram—location along the annulus is suggested.

Second: Flexion of the device so as to rotate the tip of the device away from the myocardium and towards the epicardium results in a continued sensed near field signal, which is now a larger atrial electrogram. Would diagnose location between the appendage and the ventricle. On the other hand, if such a movement results in loss of near field signals location along the annulus with now loss of contact with deflection of the catheter towards the epicardium is suggested.

If on further advancement in a cephalad direction results in only an atrial electrogram being identified, then the device is over the left atrial appendage or has advanced over the posterior left atrium/pulmonary veins. To make the distinction between these possibilities the device is moved in a septal direction (towards the pulmonary artery). With such movement if atrial electrograms are continued to be seen despite movement of more then 3 cm the initial location was likely over the posterior left atrium. However, if minimal septal movement results in loss of the atrial electrogram with either no significant electrograms being recorded or only a far field ventricular electrogram, then location overlying the left atrial appendage is suggested.

Further diagnostic information that facilitates the mapping with the electrical navigation system may be based on the differences between electrograms detected between the "jaws" of the device, closely spaced bipolar electrograms and more widely spaced electrograms—for example, with the cathode on the jaw and the anode on the shaft of the catheter. If, for example, both atrial and ventricular electrograms are seen in the widely spaced bipolar configuration but only near field atrial electrograms are seen in the closely spaced bipole distally located on the tip of the device, then the tip is likely on atrial tissue (left atrial appendage) where as the shaft remains at the junction between the appendage and the left ventricle. After deployment of the jaws (grasping tissue) if solely recorded near field electrograms are seen, grasping of atrial tissue is confirmed. On the other hand, if the widely spaced electrode configuration detects atrial electrograms but upon deployment of the grasper—now no electrograms are seen, it is likely that the device was on the atrium/appendage but pericardial or other tissue has been grasped by the device.

Pacing Stimulation:

Stimulation to pace and capture proximate myocardial tissue is performed both in a widely spaced bipolar configuration and in a closely spaced bipolar configuration—for example, between the jaws of the grasper and in some instances in a unipolar configuration. If pacing stimulation results in simultaneous atrial and ventricular capture, then either an annular location or location of the catheter between the appendage and the left ventricular myocardium is likely. The situation can be clarified by advancing and withdrawing the device with continued pacing. If persistent simultaneous atrial and ventricular capture is seen, position between the appendage and LV myocardium is likely. Whereas with advancement of atrial capture occurs and on the drawing ventricular only capture occurs, the tip of the device is likely on the mitral annuls.

If an atrial electrogram was sensed on the distal electrodes of the device and the grasper deployed, pacing stimulation is now attempted first as soon as tissue is grasped. If atrial capture does not occur then pericardial, adipose or other tissues has likely been grasped and the device is redeployed. If atrial capture occurs then the grasped tissue is withdrawn into the sheath and pacing stimulation reattempted. If atrial capture is still confirmed then the atrial appendage being grasped is confirmed.

If only atrial capture occurs from the distal bipolar electrodes but on deploying the grasper no atrial electrograms are seen on the jaw electrodes (despite atrial capture from the distal electrodes or a widely spaced electrode configuration) then left atrial tissue, atrial to the annulus but not over the left atrial appendage is likely and the device repositioned.

Arrhythmia During Device Navigation and Capture

If capture is confirmed with electrograms and pacing is noted above of left atrial appendage tissue, a ligation device is deployed. On tightening the ligature or other grasping device atrial fibrillation is noted then appendage manipulation and tightening of the ligature is likely. If on further tightening the ligature or the larger grasping device, the atrial fibrillation or other atrial arrhythmia is no longer seen, the a secure ligature etc. has been placed.

Variations of Electrogram Mapping Technique in Atrial Fibrillation

When the patient is in atrial fibrillation, sensed fibrillatory waves subplant the atrial electrogram in the descriptions above. For example, simultaneous detection of fibrillatory waves and near field ventricular electrograms would suggest deployment of the device between the appendage and overlying myocardial surface. If only fibrillatory wave electrograms are seen, the device is manipulated further cephalad. If this results in minimal fluoroscopic movements but continued sensed fibrillatory waves appendage location is likely. Pacing maneuvers to confirm appendage location would not be used during atrial fibrillation, however the presence of ventricular capture or phrenic nerve capture on the distal closely spaced bipolar shaft electrodes or jaw electrodes after the grasper has been deployed would preclude further interventions such as placing a snare or ligature over the electrical mapping device but rather result in redeployment of the angle for orientation of the device to repeat the electrogram based mapping technique.

Automated or Partially Automated Electrical Navigation

In some iterations the deflection of the sheath or grasper or when remotely steered, the target electrogram (sequence of initial ventricular electrogram followed by simultaneous atrial and ventricular electrograms followed by predominant atrial electrograms) will determine whether movement or flexion of the device occurs. That is, by an automated test movement of a few mm the atrial electrogram become smaller or less near field, then the device will no longer move or be deflected in that direction (moving away from the atrium) etc. By repetitive test movements using the criteria described above with both pacing stimulation and the sensed electrogram an automatic or partial automatic deployment towards the appendage occurs.

The complete disclosure of the patents, patent documents, and publications cited herein are incorporated by reference in their entirety as if each were individually incorporated.

Exemplary embodiments of navigation and tissue capture systems and methods have been discussed and reference has been made to possible variations. These and other variations and modifications will be apparent to those skilled in the art without departing from the scope of the invention, and it should be understood that the invention is not limited to the illustrative embodiments set forth herein. Accordingly, the invention is to be limited only by the claims provided below and equivalents thereof.

The invention claimed is:

1. A navigation and tissue capture system comprising:
   a capture device comprising a first jaw and a second jaw, wherein the first jaw and the second jaw comprise an open configuration in which the first jaw and the second jaw are open and a closed configuration in which the first jaw and the second jaw are closed, wherein an interior surface of the first jaw is located closer to an interior surface of the second jaw when the first jaw and the second jaw are in the closed configuration than when the first jaw and the second jaw are in the open configuration, wherein a primary electrode is attached to one of the first jaw and the second jaw;
   a capture shaft comprising an elongated body comprising a proximal end and a distal end, wherein the distal end of the capture shaft is attached to the capture device;
   a primary electrode attached to the capture device;
   a secondary electrode; and
   electrical monitoring apparatus operably connected to the primary electrode and the secondary electrode, wherein the electrical monitoring apparatus is configured to:
      obtain a primary signal by monitoring cardiac electrical activity using the primary electrode;
      obtain a secondary signal by monitoring cardiac electrical activity using the secondary electrode; and enhance the primary signal using the secondary signal to assist in determining the location of the capture device, wherein enhancing the primary signal comprises using the secondary signal by filtering signals from the primary signal when the secondary signal indicates ventricular activity.

2. A system according to claim 1 further comprising:
a delivery device comprising a proximal end, a distal end, and a delivery lumen comprising an opening proximate the distal end of the delivery device, wherein a longitudinal axis extends between the proximal end and the distal end, wherein the capture device and the capture shaft are sized for movement within the delivery lumen of the delivery device, wherein the capture device comprises a delivery configuration in which a distal end of the capture device is contained within the delivery lumen, wherein the capture device comprises an extended configuration in which the distal end of the capture device extends out of the delivery lumen proximate the distal end of the delivery device, wherein the secondary electrode is attached to the delivery device.

3. A system according to claim 1, wherein the electrical monitoring apparatus is configured to determine the proximity of the capture device to atrial tissue based on the primary signal and the secondary signal.

4. A system according to claim 1, wherein the electrical monitoring apparatus is configured to enhance the primary signal using the secondary signal by:
determining a ventricular time period based on the secondary signal; and
limiting monitoring of the primary signal to time periods that fall outside of the ventricular time period.

5. A system according to claim 1, wherein the electrical monitoring apparatus is configured to enhance the primary signal using the secondary signal by:
comparing the timing of the primary signal to the timing of the secondary signal; and
determining what cardiac electrical activity is detected by the primary electrode based on the comparison between the timing of the primary signal and the timing of the secondary signal;
and wherein the electrical monitoring apparatus is configured to indicate to a user that the cardiac electrical activity detected by the primary electrode comprises atrial cardiac electrical activity.

6. A system according to claim 1, wherein the electrical monitoring apparatus is configured to:
compare the timing of the P wave component of the primary signal to the timing of the P wave component of the secondary signal; and
determine what cardiac electrical activity is detected by the primary electrode based on the comparison between the timing of the P wave component of the primary signal and the timing of the P wave component of the secondary signal;
and wherein the electrical monitoring apparatus is configured to indicate to a user that the cardiac electrical activity detected by the primary electrode comprises atrial cardiac electrical activity.

7. A system according to claim 1, wherein the electrical monitoring apparatus is configured to:
compare the timing of the QRS complex component of the primary signal to the timing of the QRS complex component of the secondary signal; and
determine what cardiac electrical activity is detected by the primary electrode based on the comparison between the timing of the QRS complex component of the primary signal and timing of the QRS complex component of the secondary signal;
and wherein the electrical monitoring apparatus is configured to indicate to a user that the cardiac electrical activity detected by the primary electrode comprises atrial cardiac electrical activity.

8. A system according to claim 1, wherein the electrical monitoring apparatus is configured to:
compare the slew rate of the primary signal to the slew rate of the secondary signal; and
determine what cardiac electrical activity is detected by the primary electrode based on the comparison between the slew rate of the primary signal and the slew rate of the secondary signal;
and wherein the electrical monitoring apparatus is configured to indicate to a user that the cardiac electrical activity detected by the primary electrode comprises atrial cardiac electrical activity.

9. A system according to claim 1, wherein the electrical monitoring apparatus is configured to:
compare the relative amplitude of the primary signal to the relative amplitude of the secondary signal; and
determine what cardiac electrical activity is detected by the primary electrode based on the comparison between the relative amplitude of the primary signal and the relative amplitude of the secondary signal;
and wherein the electrical monitoring apparatus is configured to indicate to a user that the cardiac electrical activity detected by the primary electrode comprises atrial cardiac electrical activity.

10. A system according to claim 1, wherein the electrical monitoring apparatus is configured to:
compare the area under the curve of the primary signal to the area under the curve of the secondary signal; and
determine what cardiac electrical activity is detected by the primary electrode based on the comparison between the area under the curve of the primary signal and the area under the curve of the secondary signal;
and wherein the electrical monitoring apparatus is configured to indicate to a user that the cardiac electrical activity detected by the primary electrode comprises atrial cardiac electrical activity.

11. A system according to claim 1, wherein the electrical monitoring apparatus is configured to:
compare the relative shape of the primary signal to the relative shape of the secondary signal; and
determine what cardiac electrical activity is detected by the primary electrode based on comparison between the relative shape of the primary signal and the relative shape of the secondary signal;
and wherein the electrical monitoring apparatus is configured to indicate to a user that the cardiac electrical activity detected by the primary electrode comprises atrial cardiac electrical activity.

12. A system according to claim 1, wherein the electrical monitoring apparatus is configured to:
compare the slope of a selected portion of the primary signal to the slope of a selected portion of the secondary signal; and
determine what cardiac electrical activity is detected by the primary electrode based on comparison between the slope of the selected portion of the primary signal and the slope of the selected portion of the secondary signal;
and wherein the electrical monitoring apparatus is configured to indicate to a user that the cardiac electrical activity detected by the primary electrode comprises atrial cardiac electrical activity.

13. A system according to claim 1, wherein the electrical monitoring apparatus is configured to:
generate frequency domain data representative of the primary signal;
generate frequency domain data representative of the secondary signal;
compare the frequency domain data representative of the primary signal to the frequency domain data representative of the second signal; and
determine what cardiac electrical activity is detected by the primary electrode based on comparison between the frequency domain data representative of the primary signal and the frequency domain data representative of the secondary signal;
and wherein the electrical monitoring apparatus is configured to indicate to a user that the cardiac electrical activity detected by the primary electrode comprises atrial cardiac electrical activity.

\* \* \* \* \*